(12) United States Patent
Thal

(10) Patent No.: US 11,819,204 B2
(45) Date of Patent: Nov. 21, 2023

(54) ADJUSTABLE ALL-SUTURE ANCHORING ASSEMBLY AND METHOD

(71) Applicant: Raymond Thal, McLean, VA (US)

(72) Inventor: Raymond Thal, McLean, VA (US)

( * ) Notice: Subject to any disclaimer, the term of this patent is extended or adjusted under 35 U.S.C. 154(b) by 168 days.

(21) Appl. No.: 17/454,408

(22) Filed: Nov. 10, 2021

(65) Prior Publication Data

US 2022/0151602 A1    May 19, 2022

Related U.S. Application Data

(60) Provisional application No. 63/113,412, filed on Nov. 13, 2020.

(51) Int. Cl.
  *A61B 17/04* (2006.01)

(52) U.S. Cl.
  CPC .. *A61B 17/0401* (2013.01); *A61B 2017/0448* (2013.01); *A61B 2017/0464* (2013.01)

(58) Field of Classification Search
  CPC .............. A61F 2/0811; A61B 17/0401; A61B 2017/0406; A61B 2017/0409; A61B 2017/0414; A61B 2017/0458; A61B 2017/0464; A61B 2017/06185; A61B 17/06166; A61B 2017/0417; A61B 2017/0445; A61B 2017/0475; A61B 2017/044; A61B 17/0469; A61B 2017/0403; A61B 2017/0404
  See application file for complete search history.

(56) References Cited

U.S. PATENT DOCUMENTS

| | | |
|---|---|---|
| 5,569,306 A | 10/1996 | Thal |
| 5,709,788 A | 1/1998 | Chen |
| 5,782,864 A | 7/1998 | Lizardi |
| 5,891,168 A | 4/1999 | Thal |
| 6,024,758 A | 2/2000 | Thal |
| 6,319,271 B1 | 11/2001 | Schwartz et al. |
| 8,814,905 B2 | 8/2014 | Sengun et al. |
| 9,539,001 B2 | 1/2017 | Fanton et al. |
| 9,539,003 B2 | 1/2017 | Stone et al. |
| 9,724,090 B2 | 8/2017 | Kaiser et al. |
| 9,757,108 B2 | 9/2017 | Fortson |
| 9,888,997 B2 | 2/2018 | Dreyfuss et al. |
| 9,888,998 B2 | 2/2018 | Sengun et al. |
| 9,949,733 B1 | 4/2018 | Nguyen et al. |
| 2005/0187577 A1 | 8/2005 | Selvitelli et al. |
| 2006/0079904 A1 | 4/2006 | Thal |
| 2006/0190042 A1 | 8/2006 | Stone et al. |
| 2007/0083236 A1 | 4/2007 | Sikora et al. |
| 2007/0185532 A1 | 8/2007 | Stone et al. |
| 2008/0009902 A1 | 1/2008 | Hunter |

(Continued)

FOREIGN PATENT DOCUMENTS

WO    0028903 A1    5/2000

*Primary Examiner* — Katherine M Shi
(74) *Attorney, Agent, or Firm* — WELSH FLAXMAN & GITLER LLC

(57) ABSTRACT

A method and system for secure attachment of tissue to bone and other anatomical structure is disclosed. The system includes an all-suture anchor assembly including an all-suture anchor having at least one suture strand and an all-suture anchoring element threaded along the suture strand. The system also includes an adjustable self-locking device including a length of suture passing through at least one clinching portion.

6 Claims, 17 Drawing Sheets

(56) References Cited

U.S. PATENT DOCUMENTS

| | | |
|---|---|---|
| 2009/0062847 A1 | 3/2009 | Ken |
| 2009/0062854 A1 | 3/2009 | Kaiser et al. |
| 2009/0082805 A1 | 3/2009 | Kaiser et al. |
| 2009/0131947 A1 | 5/2009 | Aeschlimann et al. |
| 2010/0094425 A1 | 4/2010 | Bentley et al. |
| 2011/0022083 A1 | 1/2011 | DiMatteo et al. |
| 2011/0022084 A1 | 1/2011 | Sengun et al. |
| 2011/0270278 A1 | 11/2011 | Overes et al. |
| 2012/0071877 A1 | 3/2012 | Frigg |
| 2012/0165864 A1 | 6/2012 | Hernandez et al. |
| 2012/0197271 A1 | 8/2012 | Astorino et al. |
| 2012/0290004 A1 | 11/2012 | Lombardo et al. |
| 2012/0330357 A1 | 12/2012 | Thal |
| 2013/0110165 A1 | 5/2013 | Burkhart et al. |
| 2013/0296934 A1 | 11/2013 | Sengun |
| 2014/0081325 A1 | 3/2014 | Sengun |
| 2015/0173754 A1* | 6/2015 | Norton ............... A61B 17/0401 606/228 |
| 2015/0182215 A1 | 7/2015 | Mohamed et al. |
| 2016/0081789 A1 | 3/2016 | Denham et al. |
| 2019/0365370 A1 | 12/2019 | Thal |

\* cited by examiner

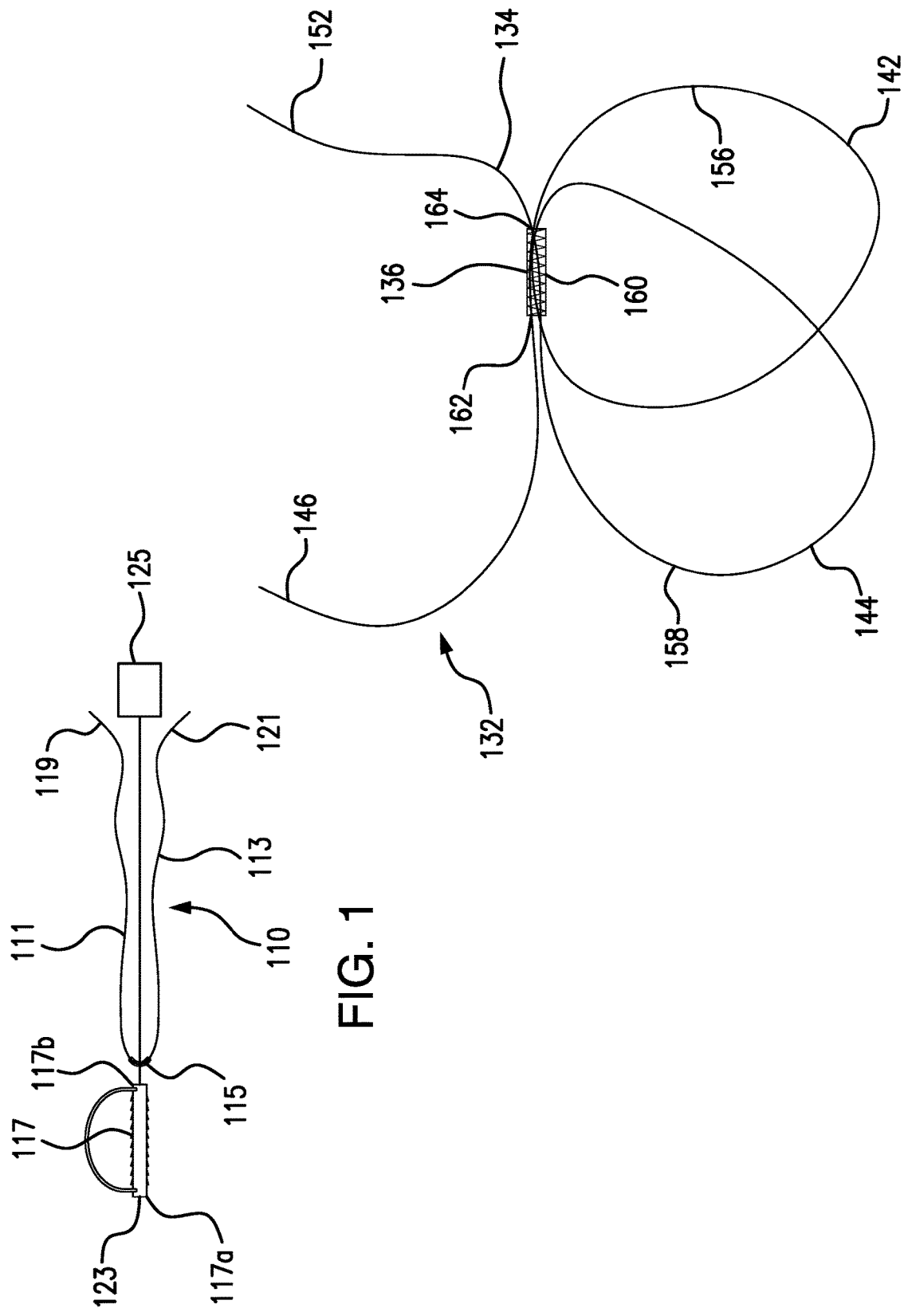

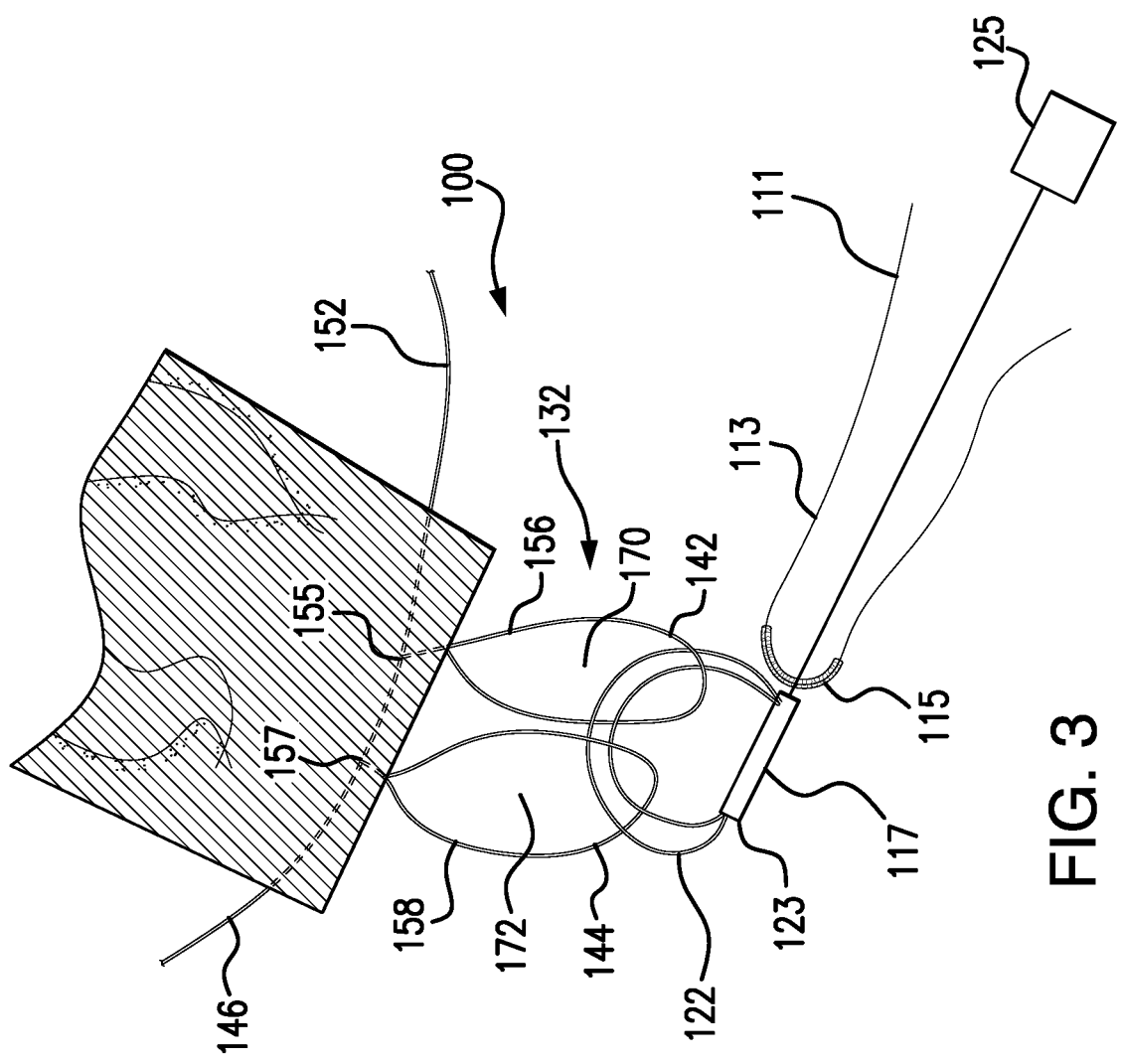

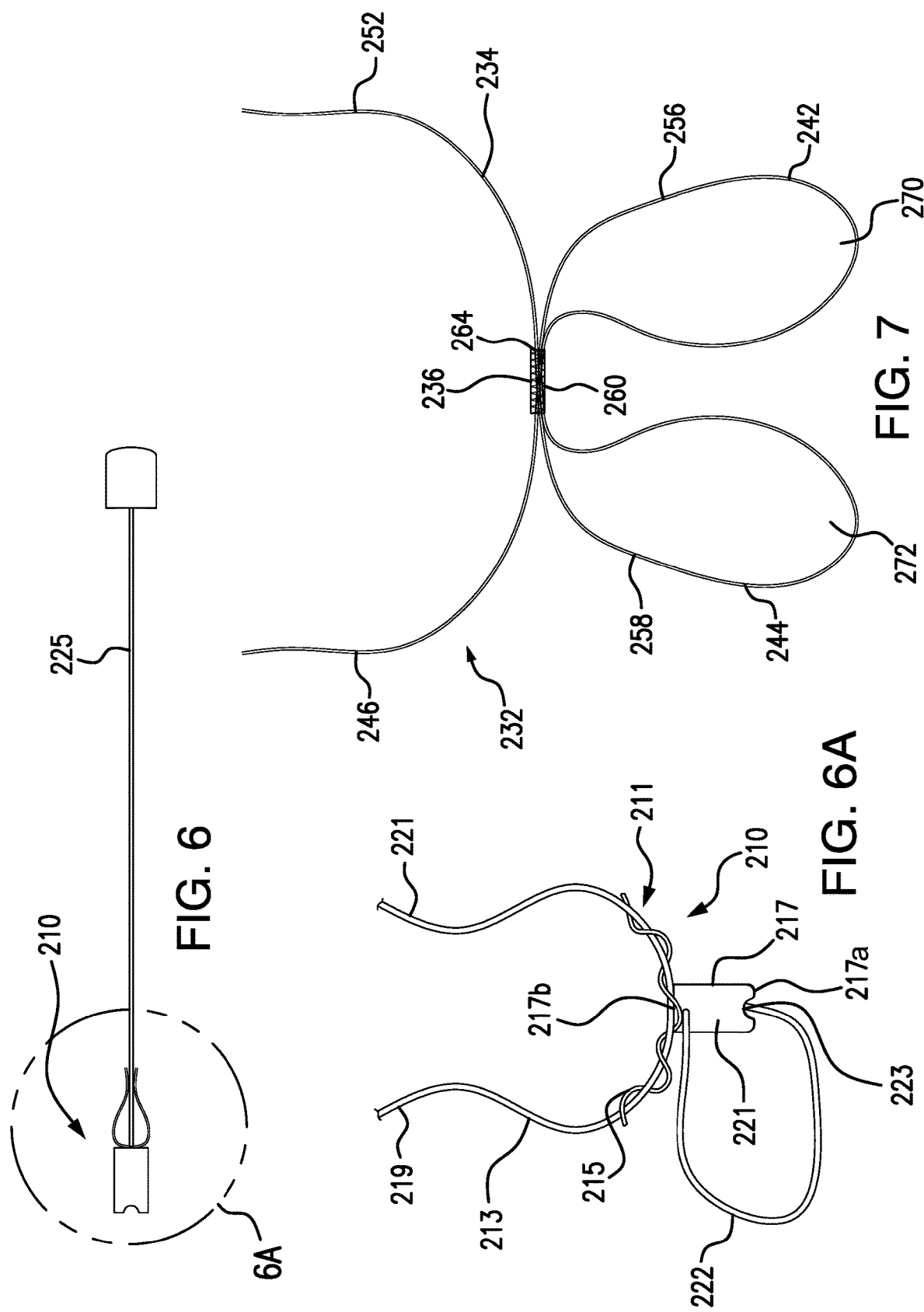

ADJUSTABLE ALL-SUTURE ANCHORING ASSEMBLY AND METHOD

CROSS REFERENCE TO RELATED APPLICATION

This application claims the benefit of U.S. Provisional Patent Application Ser. No. 63/113,412, entitled "ADJUSTABLE ALL-SUTURE ANCHORING ASSEMBLY AND METHOD," filed Nov. 13, 2020, which is incorporated herein by reference.

BACKGROUND OF THE INVENTION

1. Field of the Invention

The present invention relates to devices or methods used in tissue repair, more particularly, devices and methods for attachment of biological tissue (i.e., tendons or ligaments) to a bone mass.

2. Description of the Related Art

Soft tissues, such as tendons and ligaments, generally are attached to bone by small collagenous fibers. These connections are strong but permit the tendons and ligaments to be flexible. When a tissue, or a portion of a tissue, is torn away from the bone and requires repair, a surgeon is often required to repair the detached soft tissue with sutures, which are passed through bone tunnels and tied.

A variety of devices are available for attaching torn soft tissue to bone, such as screws, staples, cement, suture anchors. Suture anchors are commonly used to repair a torn ligament or tendon to a bone mass. These devices can be used in place of bone tunneling techniques. Suture anchors can be inserted through large open incisions or via arthroscopic surgical techniques. The arthroscope allows the surgeon to investigate a joint cavity through small incisions called portals. Various suture anchor designs are available in the market.

A suture anchor is a device that utilizes small anchors with suture materials attached thereto. A device, such as a screw, is inserted into the bone mass and anchored in place. After insertion of the anchor, the attached suture is passed through the tissue to be repaired. Recently, all-suture anchors, such as U.S. Pat. No. 9,949,733, have been developed that utilize an expandable suture or suture-based element that creates a mechanical interference under the bone surface. Sutures attached to the expandable suture element are passed through the soft tissue to facilitate the repair, in a similar fashion to the method used for repair with standard suture anchors. All-suture anchors tend to be smaller in size than standard, solid suture anchor devices. Additionally, all-suture anchors eliminate the solid anchor component that can damage joint surfaces if they inadvertently displace from the bone mass.

The tying of a knot in the suture is then required to secure the soft tissue to the bone when using either a solid suture anchor or an all-suture anchor. The process of tying a knot is time consuming and can be difficult to undertake in the tight space encountered during arthroscopic surgery and sometimes even in conventional open surgery.

Knotless anchor assemblies have been popular and are embodied in a number of prior patents such as U.S. Pat. No. 5,709,708 wherein there is provided an assembly with an anchor means having a snag means and a loop suture element attached thereto, wherein the snag means captures a loop suture element to draw tissue into secure attachment with a bone mass.

Difficulties still exist regarding the ability to adjust the tension on the repaired soft tissue. The present invention attempts to address these difficulties with a method and apparatus for knotless suture anchoring. In particular, an adjustable, knotless, all-suture anchor design is described. The present design provides for anchoring to bone using an all-suture anchor or suture-based anchor to achieve bone fixation. Tensioning of the soft-tissue repair is performed in a precise, adjustable fashion without requiring knot-tying.

SUMMARY OF THE INVENTION

In one aspect a method is disclosed for secure attachment of tissue through application of a system comprising (1) an all-suture anchor assembly including an all-suture anchor having at least one suture strand and an all-suture anchoring element threaded along the suture strand, and (2) an adjustable self-locking device including a length of suture passing through at least one clinching portion. The method includes passing the adjustable self-locking device through soft tissue to be secured to a bone mass, passing the suture strand through openings respectively defined by a first loop member and a second loop member of the adjustable self-locking device such that a free end of the suture strand is drawn through the openings such that the suture strand is intertwined or linked with the first loop member and the second loop member, and inserting the all-suture anchor assembly. The method also includes pulling, with the all-suture anchor assembly securely held, first and second ends of the suture in a manner reducing sizes of the first loop member and the second loop member and also tensioning the adjustable self-locking device, thereby drawing the soft tissue in a controlled manner. Finally, the method includes pulling the first and second ends of the suture until such a time that the soft tissue is fully pulled into position.

In some embodiments the method further includes repeating the method to provide a desired degree of tension.

In some embodiments the method further includes, after the step of pulling the first and second ends of the suture, cutting excess suture material of the first and second ends of the suture.

In some embodiments the method further includes closing an incision.

In some embodiments the method further includes, after passing the suture strand, capturing the free end of the suture strand by a capture member such that the free end of the suture strand is captured, entangled, coupled to, or otherwise attached to the capture member for manipulation of the suture strand and ultimately fixed attachment of the free end of the suture strand to the capture member upon deployment of the all-suture anchor assembly within the bone mass.

In some embodiments passing includes drawing the first loop member of the adjustable self-locking device through the soft tissue with a surgical needle.

In some embodiments the first loop member and second loop member are pulled through the soft tissue until two mounting portions defined by the first and second loop members are of substantially the same size.

In some embodiments the second loop member is passed through the soft tissue at a second location.

In some embodiments the method further includes placing the clinching portion of the adjustable self-locking device between the first loop member and the second loop member in direct contact with the soft tissue.

In some embodiments pulling includes pulling the first and second ends of the suture in a direction away from the first and second loop members causing the suture to be drawn through the adjustable self-locking device reducing the size of the first and second loop members and also tensioning the adjustable self-locking device to draw the soft tissue into position.

In another aspect a system for secure attachment of tissue to bone and other anatomical structure includes an all-suture anchor assembly including an all-suture anchor having at least one suture strand and an all-suture anchoring element threaded along the suture strand. The system also includes an adjustable self-locking device including a length of suture passing through at least one clinching portion.

In some embodiments the all-suture anchor assembly also includes a capture member for controlled capture of various elements.

In some embodiments the capture member includes an elongated body having a forward first end including a catch member and a rear second end shaped and dimensioned for selective coupling with a distal second end of a delivery inserter.

In some embodiments the catch member is a lateral slot positioned at the forward first end of the capture member.

In some embodiments the all-suture anchoring element is a cylindrical suture material or a suture tape, and a surface area of the all-suture anchoring element allows for passage of the suture strand therethrough in a manner providing for entanglement of the all-suture anchoring element and the suture strand.

In some embodiments the adjustable self-locking device includes first and second loop members that each traverse a path from one end of the clinching portion to the other end of the clinching portion.

In some embodiments a first end of the suture passes through the clinching portion and a second end of the suture passes through the clinching portion to form the first and second loop members.

In some embodiments longitudinal and parallel placement of the first and second ends of the suture within the clinching portion resists reverse relative movement of the first and second ends of the suture of the adjustable self-locking device once the adjustable self-locking device is tightened.

In some embodiments a capture member and the all-suture anchor are constructed in an integral manner.

In some embodiments the all-suture anchor assembly further includes a suture capture assembly that is integrated with the all-suture anchor.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 1 is a schematic of a delivery inserter and all-suture anchor assembly in accordance with a first embodiment.

FIG. 2 is a schematic of an adjustable self-locking device in accordance with the first embodiment.

FIGS. 3 and 4 are schematics showing use of the first embodiment.

FIG. 6 is a schematic of a delivery inserter and all-suture anchor assembly in accordance with a second embodiment.

FIG. 6A is a detailed view of the section "6A" shown in FIG. 6.

FIG. 7 is a schematic of an adjustable self-locking device in accordance with the second embodiment.

FIG. 9A is a detailed view of the section "9A" shown in FIG. 9.

FIG. 9B is a detailed view of the all-suture anchor including the suture strand, the all-suture anchoring assembly, and the suture strand loop. The all-suture anchor is shown in its undeployed state.

DESCRIPTION OF THE PREFERRED EMBODIMENTS

Figure 4:
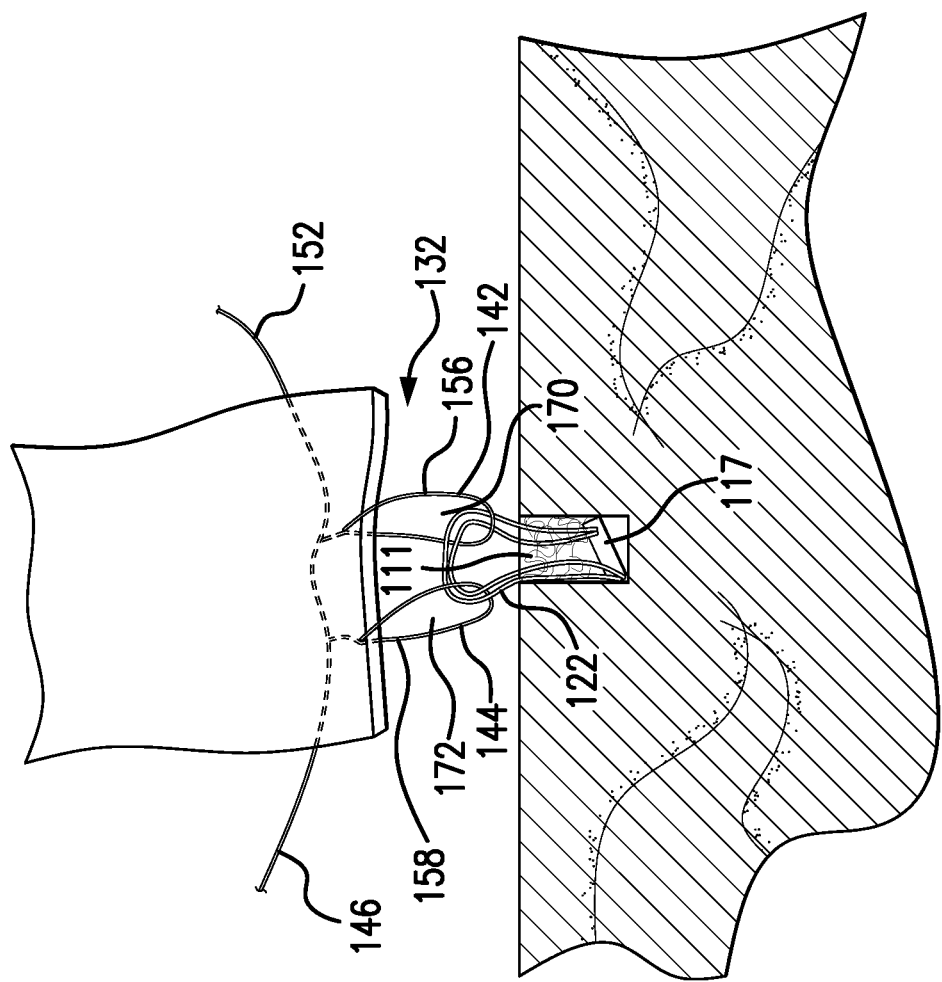

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

In accordance with the present invention, and with reference to FIGS. 1 to 4, a method and system for secure attachment of tissue to bone and other anatomical structure is disclosed. In accordance with a first embodiment as disclosed with reference to FIGS. 1 to 4, the system 100 includes an all-suture anchor assembly 110 and an adjustable self-locking device 132. As will be described below in detail, the all-suture anchor assembly 110 includes an all-suture anchor 111 composed of at least one suture strand 113 and an all-suture anchoring element 115 threaded along the suture strand 113. The suture strand 113 has a suture first end 119 and a suture second end 121. The all-suture anchor assembly 110 also includes a capture member 117 for controlled capture of various elements in a manner discussed below in greater detail.

The all-suture anchoring element 115 is preferably composed solely of an enlarged piece of cylindrical suture material or a suture tape. The enlarged surface area of the all-suture anchoring element 115 allows for the passage of the suture strand 113 therethrough in a manner providing for entanglement of the all-suture anchoring element 115 and the suture strand 113. The suture anchoring element 115 includes a first end and a second end, as well as a thickness, a width, and a length along a longitudinal axis.

As briefly mentioned above, the all-suture anchor assembly 110 includes the suture strand 113, which is passed through, or weaved through, the all-suture anchoring element 115 at various locations along the length of the all-suture anchoring element 115 (so as to define the all-suture anchor 111). That is, the suture strand 113 penetrates and traverses the all-suture anchoring element 115 to define apertures in the all-suture anchoring element 115. The intersections of the suture strand 113 with the all-suture anchoring element 115 are referred to herein as suture aperture locations and, as such, each of the suture aperture locations is a location where the suture strand 113 passes through the thickness of the all-suture anchoring element 115. While the suture aperture locations disclosed in accordance with a preferred embodiment are all centrally located along the all-suture anchoring element 115 so as to be oriented along the central longitudinal axis of the all-suture anchoring element 115, it is appreciated the suture aperture locations may be varied (for example, staggered on opposite sides of the central longitudinal axis of the all-suture anchoring element) without departing from the spirit of the present invention. In accordance with a preferred embodiment, the all-suture anchoring element may have various length and width dimensions depending upon the purpose for which it is intended.

It should be appreciated the above description of the preferred structure of the all-suture anchoring element 115 is as "an enlarged piece of cylindrical suture material or a suture tape". Note that the all-suture anchoring element of some commercially available all-suture anchors have a structure that is like a sock. The suture strand is weaved through the all-suture anchoring "sock" element.

Regardless of the structure of the all-suture anchoring element, the all-suture anchoring element is inserted into the bone in an undeployed state. This undeployed state is usually "elongated." The all-suture anchoring element is deployed (expanded) after insertion into the bone mass. The undeployed all-suture anchoring element can be inserted into the bone after a drill hole has been established or the undeployed all-suture anchoring element can be directly inserted into the bone. When the all-suture anchoring element is inserted directly into the bone, without a prior drill hole, often a "spike-tipped inserter" creates an opening in the bone for insertion of the all-suture anchoring element. Also note that there are several methods used for deployment of the all-suture anchoring element, regardless of the structure (cylindrical suture material, suture tape, or sock). Deployment can be achieved by pulling on the suture strand(s). Alternatively, a separate "deployment strand" is attached to or weaved to the all-suture anchoring element. This "deployment strand" can be pulled or tensioned to deploy the all-suture anchoring element. Additionally, mechanical systems have been developed that provide tension on the deployment suture, to deploy the all-suture anchoring element. Also note that all-suture anchor systems may have one or more suture strands. After deployment of the all-suture anchoring element, the suture strand(s) can slide within the all-suture anchoring element to facilitate knot-tying. Alternatively, the suture strand(s) may not slide after deployment of the all-suture anchoring element.

With the foregoing in mind, it is appreciated that a large variety of constructions and materials will work for the all-suture anchoring element. For example, the all-suture anchor may take a variety of forms as known in the art, for example, ConMed Y-Knot® & Y-Knot® RC, Parcus Draw Tight™, Smith & Nephew Suturefix Ultra, Smith & Nephew Q-FIX®, Zimmer Biomet: JuggerKnot® Soft Anchor; Cayenne Medical (Zimmer Biomet company) SureLock®, and Stryker® Iconix. It has been discovered that for each type of construction (i.e., braided, woven, non-woven, or knitted) it is advantageous to use a material that increases in width for every reduction in length. This advantageously provides for increased diameters for a particular number of folds, pleats, crinkles, or other changes in the shape of the all-suture anchoring element. Regardless of the material chosen for use in accordance with the present invention, the material must exhibit desirable deformation and retention characteristics.

The all-suture anchor assembly 110 further includes a solid capture member 117 that is separate and distinct from the all-suture anchor 111 as disclosed in accordance with this embodiment. The capture member 117 is merely attached to the distal end of the delivery inserter 125. However, it is appreciated the capture member may be integrated with the all-suture anchor 111 as disclosed below with reference to FIGS. 6 to 8.

The capture member 117 may be composed of a variety of biocompatible materials (for example, biocompatible polymers) known to those skilled in the art. In accordance with a preferred embodiment, the solid capture member 117 includes an elongated body having a forward first end 117a and a rear second end 117b. Functionality in conjunction with the capture member 117 may be further enhanced by the provision of spikes or ridges along the outer surface thereof.

While the capture member may be integrated with or separate/distinct from the all-suture anchor, it should be appreciated the delivery and use thereof would be substantially the same.

The forward first end 117a also includes a catch member 123. In accordance with a disclosed embodiment, the catch member 123 is a lateral slot positioned at the forward first end 117a of the capture member 117. While the lateral slot 123 is shown at the forward first end 117a in accordance with the disclosed embodiment, it is appreciated the lateral slot 123 could be positioned at various locations along the capture member 117 so long as the lateral slot 123 is able to engage a suture strand loop 122 for operation in accordance with the present invention. The catch member 123 is shaped and dimensioned for capture and retention of suture(s), in particular, the suture strand loop 122, as discussed below in greater detail. While the catch member 123 is disclosed herein as being a lateral slot, it is appreciated the catch member 123 may take a variety of forms so long as it is capable of catching or snagging the suture strand loop 122, and therefore may take various shapes and have various dimensions without departing from the spirit of the present invention; for example, the catch member 123 may be shaped in the form of a hook, or other type projection, or a recess cut into the capture member 117, or a slit cut into an existing opening in the capture, for engaging the continuous loop of the suture strand loop 122.

The rear second end 117b of the capture member 117 is shaped and dimensioned for selective coupling with a distal second end of the delivery inserter 125, for example, via a threaded attachment structure. In accordance with a preferred embodiment, the delivery inserter 125 includes an elongated body with a proximal first end and a distal second end. The proximal first end is provided with a handle for actuation in accordance with the present invention. The distal second end is shaped and dimensioned for selective attachment to the capture member 117. Such delivery inserters, and in particular, compression mechanisms, are known within the art, for example, see the Draw Tight™ Suture Based Anchor System as manufactured by Parcus, and the delivery inserters of ConMed as used with Y-Knot® all-suture anchors (both of which hold the all-suture anchor inserter on a "rod-like" inserter), as well as the Smith-Nephew Q-fix inserter (that utilizes a tube-shaped inserter and the all-suture anchor is pushed out of the tube upon deployment), The delivery inserter 125 is operated by a surgeon whereby the surgeon manipulates the all-suture anchoring element 115 and the suture strand 113. The surgeon inserts the capture member 117, the all-suture anchoring element 115, and the entangled portion of the suture strand 113 in the bone hole by pushing the distal second end of the delivery inserter 125 into the bone hole. At that point, the surgeon can push a button or turn a device on the delivery inserter 125 which enables the deployment of the all-suture anchoring element 115. While a push-button or twisting mechanism is disclosed above for deployment of the all-suture anchoring element 115, it is appreciated other known mechanisms (for example, pulling a deployment suture) for all-suture anchors may be employed without departing from the spirit of the present invention. The all-suture anchoring element 115 is then folded, bent, creased, crinkled, bunched, or otherwise changed in shape after it is inserted into the bone hole in a manner that increases the size of the all-suture anchoring element 115 in a direction substantially perpendicular to the longitudinal axis of the bone hole to develop an outwardly directed force that is directed at the walls of the bone hole. The folding, bending, creasing, crinkling, bunching, or other changes in the shape of the all-suture anchoring element 115 is achieved using known techniques.

The suture strand 113, the all-suture anchoring element 115, and the capture member 117 are installed within the bone hole in an elongated fashion to take advantage of a small diameter configuration, referred to herein as an undeployed state or installation state. Deployment occurs after the delivery inserter 125 is manipulated such that the capture member 117 captures and retains the suture strand loop 122. This capture and retention are followed by positioning of the suture strand 113, the all-suture anchoring element 115, and the capture member 117 within a bone hole for retention of the various elements to a bone mass.

In particular, the all-suture anchoring element 115 is deployed causing the all-suture anchoring element 115 to fold, bend, crease, crinkle, bunch or otherwise change shape in a manner that compresses the all-suture anchoring element 115. It is appreciated that deployment may occur before, after, or as the delivery inserter 125 is removed. As the all-suture anchoring element 115 is compressed in this manner it ultimately increases in size in a direction substantially perpendicular to the longitudinal axis of the bone hole (or otherwise oriented to contact side walls of the bone hole) and develops an outwardly directed force that is directed at the walls of the bone hole. As such, and after the delivery inserter 125, or other delivery instrument, has been removed, the all-suture anchoring element 115 exhibits an outward bias resulting in expansion of the all-suture anchoring element 115 in a direction substantially perpendicular to the longitudinal axis of the bone hole (or otherwise oriented to contact side walls of the bone hole) into which it is positioned, resulting in frictional engagement or gripping the wall of the bone, which is referred to herein as the expanded deployed state.

The all-suture anchoring element 115 is folded or otherwise compressed to form pleats between adjacent suture aperture locations. This pleating reduces the distance between the first suture aperture location and the second suture aperture location, as measured along the length of the all-suture anchoring element 115. These pleats form a bunched mass of suture material effectively increasing a diameter, or cross-sectional dimension, (as measured in relation to the axis of the bone hole) of the all-suture anchoring element 115, which ultimately causes the all-suture anchor assembly 110 to displace cancellous bone or lock beneath the bone cortex. The relative increase in the cross-sectional size of the all-suture anchoring element 115 in the direction substantially perpendicular to the longitudinal axis of the bone hole (or in another direction to facilitate contact of the all-suture anchoring element 115 with the side walls of the bone hole) creates a retention force of the all-suture anchor assembly 110. Additional retention force can be achieved when the all-suture anchor assembly is deployed beneath the bone cortex.

It is appreciated that a mechanical tensioning mechanism, as is well known to those skilled in the art, may be used during the deployment of the all-suture anchoring element 115. Such mechanical tensioning mechanisms pull or ratchet the suture while the delivery inserter 125 holds the all-suture anchoring element 115 in place. Mechanical tensioning, of this nature, may be preferable as this can more tightly 'fold' or 'bunch' the all-suture anchoring element 115, thereby increasing the created tension, that is, the outward force of the all-suture anchoring element 115, which is relative to the longitudinal axis of the bone hole and toward the walls of the bone hole, resulting from increased compression of the all-suture anchoring element 115. The changed shape of the all-suture anchoring element 115 provides security within the bone, for example, below the cortical layer.

It should be appreciated that the relative fit of the all-suture anchor 111 in the bone hole in its deployed configuration is shown as being relatively "loose." This is done to provide a clear view for the elements making up the present invention. In practice, it is appreciated that the suture, all-suture anchoring element 115, the capture member 117, a portion of the suture strand 113, and delivery inserter 125 would be tightly pressed into the bone hole, as any excess space would need to be taken up by the expansion of the all-suture anchor 111 in a direction substantially perpendicular to the longitudinal axis of the bone hole (or otherwise oriented to contact side walls of the bone hole).

The present invention achieves secure, tensioned attachment of soft tissue to a bone mass using the all-suture anchor assembly 110 as described above in conjunction with the adjustable self-locking device 132 composed of a length of suture 134 passing through one or more clinching portion(s) 136. In such a way that first and second suture loop members 142, 144 are created.

With reference to FIG. 2, a preformed adjustable self-locking device 132 is disclosed. The adjustable self-locking device 132 is preformed to include a double loop configuration having first and second loop members 142, 144 that each traverse a path from one end of the clinching portion 136 to the other end thereof. The adjustable self-locking device 132 is formed by passing the first end 146 of the suture through the clinching portion 136 and similarly passing the second end 152 through the clinching portion 136. In various aspects, the passageway defined by the clinching portion 136 is formed during a braiding process.

Passing ends 146, 152 through the passageway defined by the clinching portion 136 forms the first and second loop members 142, 144. The first and second loop members 142, 144 define mounting portions 156, 158 of the adjustable self-locking device 132 and can be disposed generally opposite from the clinching portion 136.

The longitudinal and parallel placement of the first and second ends 146, 152 of the suture 134 within the clinching portion 136 resists the reverse relative movement of the first and second ends 146, 152 of the adjustable self-locking device 132 once it is tightened. The tensioning of the first and second ends 146, 152 causes reciprocal movement of the first and second loop members 142, 144 relative to clinching portion 136. Upon applying tension to the first and second ends 146, 152, the first and second loop members 142, 144 are reduced to a desired size or placed in a desired tension. Tension in the first and second loop members 142, 144 causes the body of the suture defining the clinching portion 136 to be placed in tension and therefore cause the clinching portion 136 to constrict about the portions 162, 164 of the suture 134 passing through the passageway defined by the clinching portion 136. This constriction causes the adjustable self-locking device 132 to "automatically" lock in a reduced size or smaller diameter configuration for the two loop members 142, 144.

In accordance with the present method, the adjustable self-locking device 132 is first passed through the soft tissue one wishes to secure to a bone mass. Referring to FIG. 3, the adjustable self-locking device 132, in particular, the first loop member 142 thereof is drawn through the soft tissue with a surgical needle. A variety of suture passing methods can be used such as arthroscopic suture passers, arthroscopic suture shuttling devices or suture, or the like. In particular, the first loop member 142 and second loop member 144 are pulled through the soft tissue until the two mounting portions 156, 158 defined by the first and second loop members 142, 144 are of substantially the same size or different sizes and in alignment. The first loop member 142 is passed through the soft tissue at a first location 155. The second loop member 144 is passed through the soft tissue at a second location 157. In particular, the first loop member 142 and second loop member 144 are pulled through the soft tissue until the two mounting portions 156, 158 defined by the first and second loop members 142, 144 are of substantially the same size and in alignment. Pulling the first and second loop members 142, 144 through the tissue is preferably achieved using a "utility suture" in a manner known to those skilled in the art. It is appreciated the first and second loop members 142, 144 are relatively long so that the opposed mounting portions 156, 158 may be brought outside of the joint under repair. As shown in FIGS. 3, the first and second end 146, 152 of the suture 134, which function as tension members as will be discussed below in greater detail, of the adjustable self-locking device 132 also extends from one of the first and second loop members 142, 144 and are similarly accessible from outside of the joint under repair. (Note that this self-locking device 132 can have just one loop member 142, without a second loop member 144. Alternatively, the self-locking device can have more than 2 adjustable loops. When using the described self-locking device (with 2 loop members 142 & 144), an alternative method would be to only pass one loop member (i.e., loop member 142) and not pass loop member 144 through the soft tissue. Both loops would still be captured by capture member 117.

With the first and second loop members 142, 144 of the adjustable self-locking device 132 outside of the joint, and with reference to FIG. 3, the suture strand loop 122 of the capture member 117 is passed through the openings 170, 172 respectively defined by the opposed first and second loop members 142, 144. That is, the free end of the suture strand loop 122 is drawn through the openings 170, 172 such that the suture strand loop 122 is intertwined or linked with the opposed first and second loop members 142, 144. In this arrangement, the clinching portion 136 of the adjustable self-locking device 132 between the first and second loop members 142, 144 is in direct contact with the soft tissue securing the suture strand loop 122 to the soft tissue such that the first and second loop members 142, 144 may simultaneously pull against the suture strand loop 122 without fear that the adjustable self-locking device 132 will become disengaged with the soft tissue. Alternatively, the first and second loop members 142, 144 can be captured by independent all-suture anchor assemblies 110 and secured to separate locations on the bone.

Thereafter, the free end of the suture strand loop 122 is captured by the catch member 123 of the capture member 117; that is, the free end of the suture strand loop 122 is captured, entangled, coupled to, or otherwise attached to the catch member 123 at the first end of the capture member 117 for manipulation of the suture strand loop 122 and ultimately fixed attachment of the free end of the suture strand loop 122 to the catch member 123 at the first end of the capture member 117 upon deployment of the all-suture anchor assembly 110 within the bone mass. It is appreciated that if the catch member 123 is not positioned at the first end of the capture member 117, the free end of the suture strand loop 122 would be fixed wherever the catch member 123 is located.

With the suture strand loop 122 passed through the openings 170, 172 defined by the opposed first and second loop members 142, 144 and the free end of the suture strand loop 122 captured by the catch member 123 at the first end of the capture member 117, the suture strand loop 122 is linked to the first and second loop members 142, 144 and ultimately the soft tissue. Referring to FIG. 4, the all-suture anchor assembly 110 is then inserted within an anchor hole preferably predrilled in the bone mass. The provision of the clinching portion 136 with the suture portions 162, 164 therethrough and under the control of the first and second ends 146, 152 of the suture 134, provides for adjustment in the size of the first and second loop members 142, 144. This adjustability is useful in several aspects of the surgical procedure.

With the all-suture anchor assembly 110 securely held within the drill hole, the first and second ends 146, 152 of the suture 134 are pulled in a manner reducing the sizes of the first and second loop members 142, 144, and also tensioning the adjustable self-locking device 132, thereby drawing the soft tissue toward the bone mass in a controlled manner. It should be appreciated the ability to reduce the size of the first and second loop members 142, 144 relative to the suture strand loop 122 is permitted as a result of the fact that the engagement point for the first and second loop members 142, 144, and the suture strand loop 122 sits above the bone hole or within the bone hole, but above the deployed all-suture anchoring element 115 and there is no impediment to the free movement of the first and second loop members 142, 144 relative to the suture strand loop 122.

In particular, the first and second ends 146, 152 are pulled in a direction away from the first and second loop members 142, 144 causing the suture 134 to be drawn through the adjustable self-locking device 132 reducing the size of the first and second loop members 142, 144, and also tensioning the adjustable self-locking device 132 to lock the suture portions 162, 164 therein, and consequently drawing the soft tissue toward the bone mass since the size of the suture strand loop 122 is fixed. The first and second ends 146, 152 of the suture 134 are pulled and the sizes of the first and second loop members 142, 144 are reduced until such a time that the soft tissue is fully pulled toward the bone mass. The procedure may be repeated to provide the desired degree of tension on the repair. The excess suture material of the first and second ends 146, 152 of the suture 134 may then be cut away and the incision closed.

Referring to FIG. 4, it is also appreciated that the present invention allows for anchoring and soft tissue attachment with limited regard for the depth of the drilled hole or the depth of the all-suture anchor assembly 110 within the bone mass. This results from the ability to draw the soft tissue toward the all-suture anchor assembly 110 and bone mass under the control of the adjustable self-locking device 132, in particular pulling of the first and second ends 146, 152 of the suture 134 which results in a reduction in the size of the loop members 142, 144. Because the size of the loop members 142, 144 dictate how close the soft tissue is pulled toward the bone mass/bone anchor, a medical practitioner can readily control the position of the soft tissue relative to the bone mass/bone anchor and control the tension applied to the repair.

Figure 5:
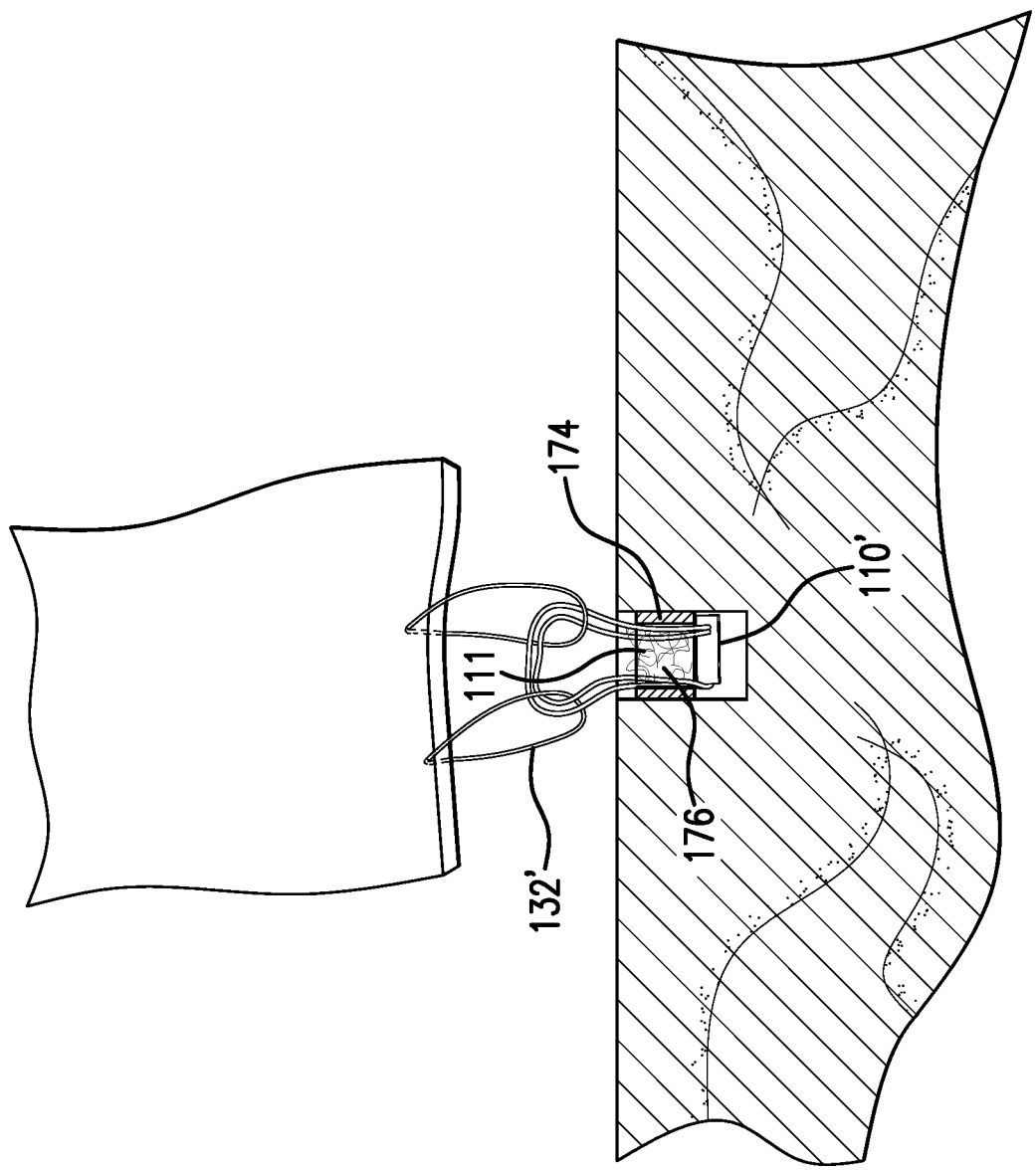
FIG. 5 is a schematic showing use of the first embodiment with a sleeve.

With reference to FIG. 5, an alternate embodiment is disclosed that is similar to that disclosed with reference to FIGS. 1 to 4. In the alternate embodiment, a cylindrical anchor mounting sleeve 174 is employed for secured attachment of the all-suture anchor assembly 110. The distal end of the cylindrical anchor mounting sleeve 174 is open, allowing access to the internal bone mass. Any fixation method can be utilized to affix the anchor mounting sleeve to the bone mass. In fact, standard suture anchors, and insertion methods, are known for deployment of a hollow, threaded sleeve, with attached sutures. For example, the DePuy/Synthes—Mitek Healix suture anchor or the Smith & Nephew Healicoil suture anchor both consist of a cylindrical, threaded anchor body with attached suture. These cylindrical anchors, without the attached suture, could function as the anchor mounting sleeve. It is appreciated the open cylindrical anchor mounting sleeve 174 provides an anchor recess (or anchor passageway 176 in accordance with such an embodiment) extending from the proximal end of the open cylindrical anchor mounting sleeve 174 to the distal end of the open cylindrical anchor mounting sleeve 174.

The anchor passageway 176, in the open cylindrical anchor mounting sleeve 174, allows for capture of the all-suture anchor assembly 110 on the distal end of the open cylindrical anchor mounting sleeve 174 within a small cavity defined by the bottom of the anchor hole and the distal end of the open cylindrical anchor mounting sleeve 174. The all-suture anchor assembly 110 is passed through the anchor passageway 176 with the longitudinal axis of the all-suture anchor assembly 110 aligned substantially parallel with the longitudinal axis of the open cylindrical anchor mounting sleeve 174 (see FIG. 5). Once the all-suture anchor assembly 110 has passed fully through the anchor passageway 176 and distal to the end of the open cylindrical anchor mounting sleeve 174, the all-suture anchor assembly 110 is deployed as described above to thereby lock the all-suture anchor assembly 110 in position due to the fact the length of the all-suture anchor assembly 110 is greater than the diameter of the anchor passageway 176. The fixation method of the cylindrical anchor mounting sleeve (i.e.—external threads) provides secure bone fixation. It is also appreciated, the internal structure of the bone mass is not very dense and the all-suture anchor assembly 110 may actually be pushed into, and manipulated within the bone mass for orientation, thereby obviating the need for a deep hole or a hole extending below the distal end of the open cylindrical anchor mounting sleeve 174.

Once the all-suture anchor assembly 110 is locked in position distal to the anchor mounting sleeve 174, the adjustable self-locking device 132 may be tightened as discussed above with regard to FIGS. 1 to 4.

As mentioned above, the capture member and the all-suture anchor may be constructed in an integral manner. Such an embodiment is disclosed in FIGS. 6 to 8. In particular, the all-suture anchor assembly 210 includes an all-suture anchor 211 composed of at least one suture strand 213 and an all-suture anchoring element 215 threaded along the suture strand 213 in manner discussed above with reference to the embodiment disclosed in FIGS. 1 to 4. The all-suture anchor assembly 210 also includes a capture member 217 integrated with the at least one suture strand 213 and/or the all-suture anchoring element 215 for controlled capture of various elements in a manner discussed below in greater detail. The suture strand 213 has a suture first end 219 and a suture second end 221.

The all-suture anchoring element 215 is preferably composed solely of an enlarged piece of cylindrical suture material, a suture tape, or suture sock. The enlarged surface area of the all-suture anchoring element 215 allows for the passage of the suture strand 213 therethrough in a manner providing for entanglement of the all-suture anchoring element 215 and the suture strand 213. As mentioned above, and as well appreciated by those skilled in the art, a large variety of constructions and materials will work for the all-suture anchoring element. For example, the all-suture anchor may take a variety of forms as known in the art, for example, ConMed Y-Knot® & Y-Knot® RC, Parcus Draw Tight™, Smith & Nephew Suturefix Ultra, Smith & Nephew Q-FIX®, Zimmer Biomet: JuggerKnot® Soft Anchor; Cayenne Medical (Zimmer Biomet company) SureLock®, and Stryker® Iconix.

The all-suture anchor assembly 210 further includes the solid capture member 217 that is integrated onto the all-suture anchoring element 215. Those skilled in the art will appreciate, the capture member 217 may be composed of a variety of biocompatible materials (for example, biocompatible polymers) known to those skilled in the art. In accordance with a preferred embodiment, the solid capture member 217 includes an elongated body having a forward first end 217*a* and a rear second end 217*b*. The capture member 217 is preferably secured to the all-suture anchoring element 215 by passing the all-suture anchoring element 215 through a lateral aperture formed in the capture member 217. While FIGS. 6 to 8 disclose the all-suture anchoring element 215 passing through the capture member 217, it is appreciated other mechanisms for integrating the capture member 217 with the suture strand 213 and/or the all-suture anchoring element 215 may be employed. For example, the suture strand might be passed through the lateral aperture, or both the suture strand and the all-suture anchoring element may be passed through the lateral aperture. Functionality in conjunction with the capture member 217 may be further enhanced by the provision of spikes or ridges along the outer surface thereof. As mentioned above, delivery and use of the suture strand 213, the all-suture anchoring element 215, and the capture member 217 would be substantially the same as the attached version and only the attached version will be described below in detail.

The forward first end 217*a* of the capture member 217 also includes a catch member 223. In accordance with a disclosed embodiment, the catch member 223 is a lateral slot positioned at the forward first end 217*a* of the capture member 217. While the lateral slot 223 is shown in accordance with the disclosed embodiment, it is appreciated the lateral slot 223 could be positioned at various locations along the capture member 217 so long as the lateral slot 223 is able to engage the suture strand loop 222 for operation in accordance with the present invention. The catch member 223 is shaped and dimensioned for capture and retention of suture(s), in particular, a suture strand loop 222, as discussed below in greater detail. While the catch member 223 is disclosed herein as being a lateral slot, it is appreciated the catch member 223 may take a variety of forms so long as it is capable of catching or snagging the suture strand loop 222, and therefore may take various shapes and have various dimensions without departing from the spirit of the present invention; for example, the catch member 223 may be shaped in the form of a hook, or other type projection, or a recess cut into the capture member 217, or a slit cut into an existing opening in the capture, for engaging the continuous loop of a suture strand loop 222.

The rear second end 217b of the capture member 217 is shaped and dimensioned for selective coupling with a distal second end of the delivery inserter 225, for example, via a threaded attachment structure. In accordance with a preferred embodiment, the delivery inserter 225 includes an elongated body with a proximal first end and a distal second end. The proximal first end is provided with a handle for actuation in accordance with the present invention. The distal second end is shaped and dimensioned for selective attachment to capture member 217. Such delivery inserters, and in particular, compression mechanisms are known within the art, for example, see the Draw Tight™ Suture Based Anchor System as manufactured by Parcus and the delivery inserters of ConMed as used with Y-Knot® all-suture anchors, and various compression mechanisms may be used within the spirit of the present invention.

The delivery inserter 225 is operated by a surgeon whereby the surgeon manipulates the all-suture anchoring element 215 and the suture strand 213. The surgeon inserts the capture member 217, the all-suture anchoring element 215, and the entangled portion of the suture strand 213 in the bone hole by pushing the distal second end of the delivery inserter 225 into the bone hole. At that point, the surgeon can push a button or turn a device on the delivery inserter 225 which enables the deployment of the all-suture anchoring element 215 (different methods of deployment are discussed above). While a push-button or twisting mechanism is disclosed above for deployment of the all-suture anchoring element 215, it is appreciated other known mechanisms (for example, pulling a deployment suture) for all-suture anchors may be employed without departing from the spirit of the present invention. The all-suture anchoring element 215 is then folded, bent, creased, crinkled, bunched or otherwise changed in shape after it is inserted into the bone hole in a manner that increases the size of the all-suture anchoring element 215 in a direction substantially perpendicular to the longitudinal axis of the bone hole to develop an outwardly directed forced that is directed at the walls of the bone hole. The folding, bending, creasing, crinkling, bunching or other changes in the shape of the all-suture anchoring element 215 is achieved using known techniques.

The suture strand 213, the all-suture anchoring element 215, and the capture member 217 are installed within the bone hole in an elongated fashion to take advantage of a small diameter configuration, referred to herein as an undeployed state or installation state. Deployment occurs after the delivery inserter 225 is manipulated such that the capture member 217 captures and retains suture strand loop 222. This capture and retention are followed by positioning of the suture strand 213, the all-suture anchoring element 215, and the capture member 217 within a bone hole for retention of the various elements to a bone mass.

Figure 8:
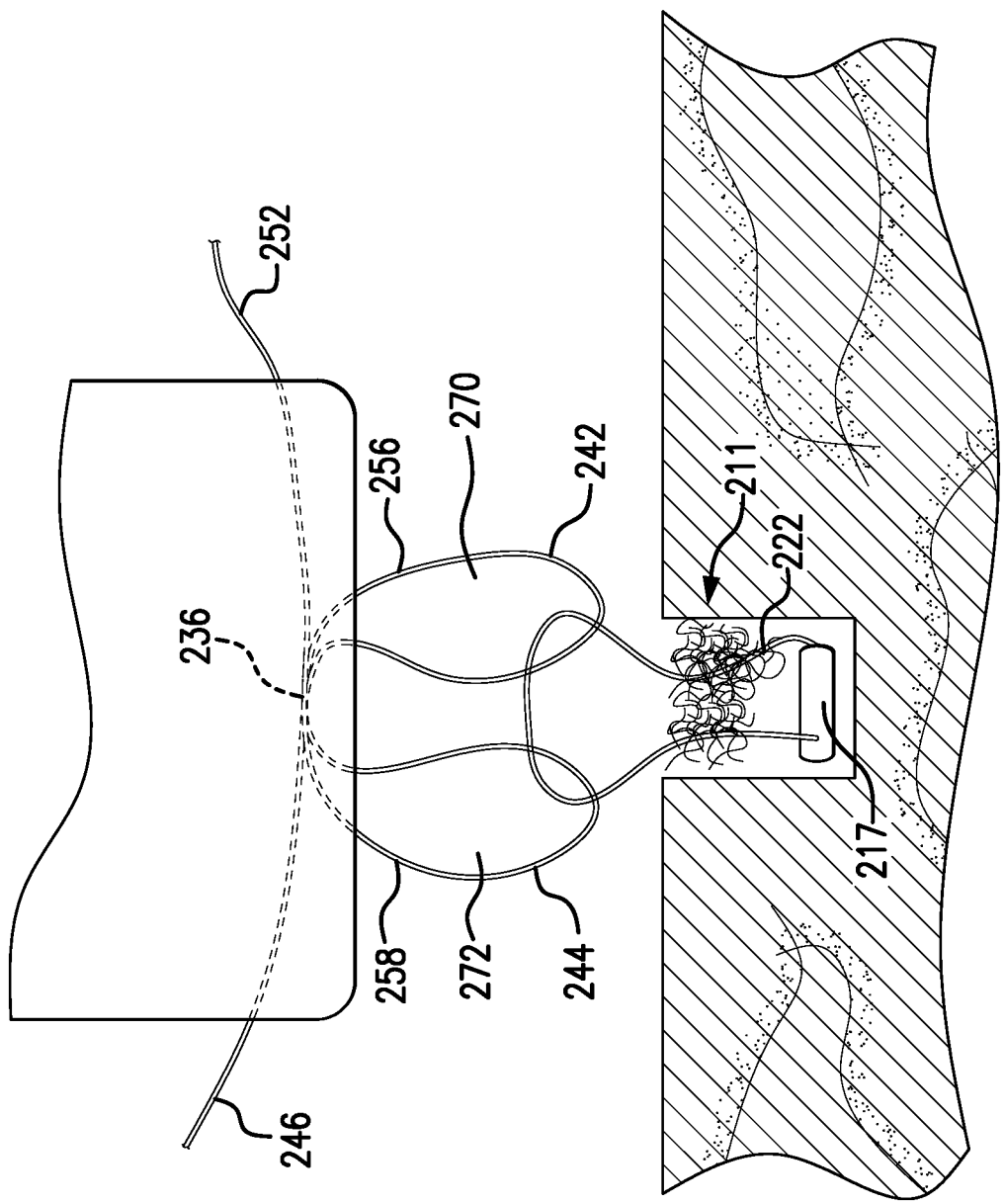
FIG. 8 is schematic showing use of the second embodiment.
Figure 9:
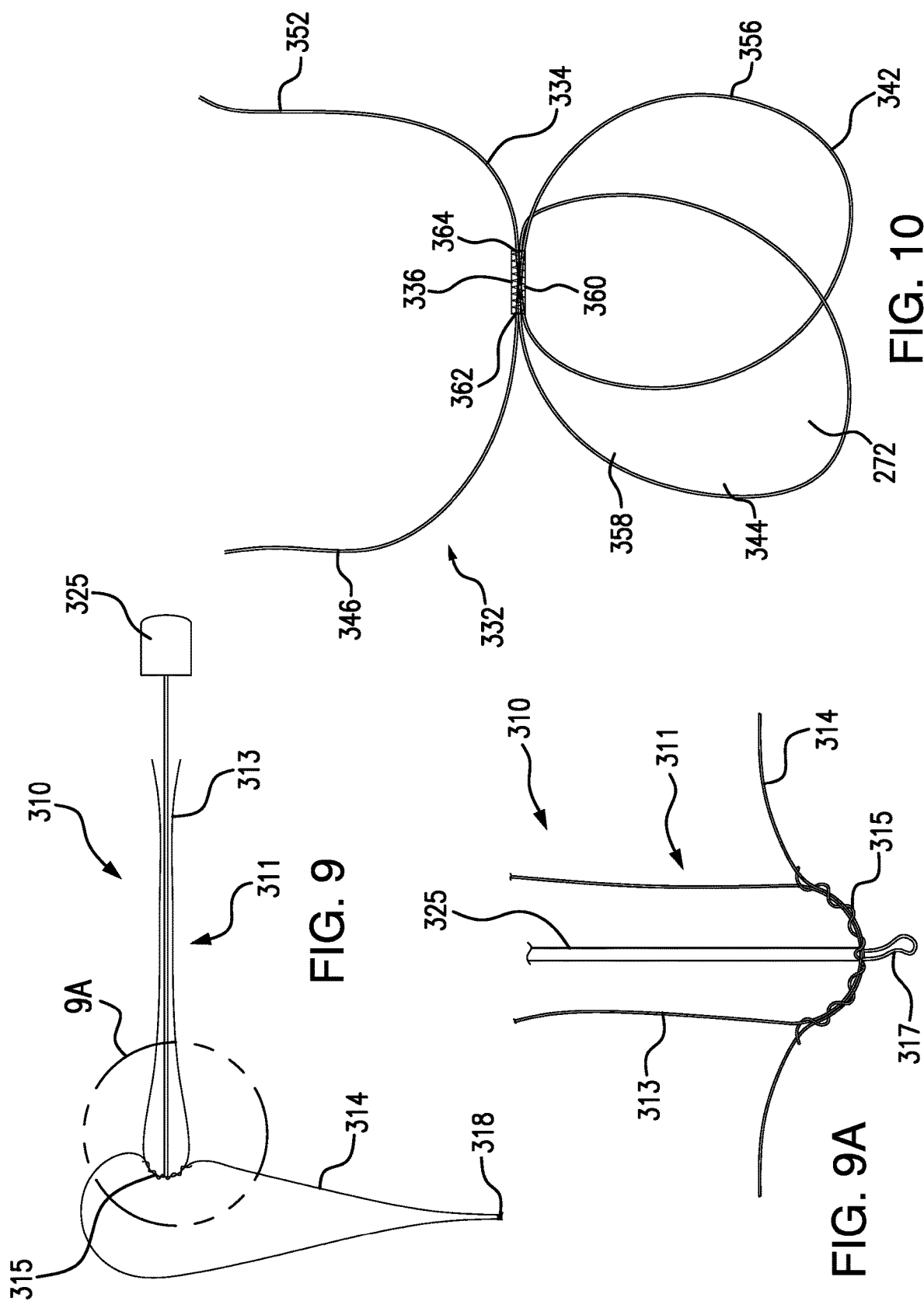
FIG. 9 is a schematic of a delivery inserter and all-suture anchor assembly in accordance with a third embodiment.

In particular, and as disclosed with the embodiment of FIG. 8, the all-suture anchoring element 215 is deployed causing the all-suture anchoring element 215 to fold, bend, crease, crinkle, bunch or otherwise change shape in a manner that compresses the all-suture anchoring element 215. It is appreciated that deployment may occur before, after, or as the delivery inserter 225 is removed. As the all-suture anchoring element 215 is compressed in this manner it ultimately increases in size in a direction substantially perpendicular to the longitudinal axis of the bone hole (or otherwise oriented to contact side walls of the bone hole) and develops an outwardly directed force that is directed at the walls of the bone hole. As such, and after the delivery inserter 225, or other delivery instrument, has been removed, the all-suture anchoring element 215 exhibits an outward bias resulting in expansion of the all-suture anchoring element 215 in a direction substantially perpendicular to the longitudinal axis of the bone hole (or otherwise oriented to contact side walls of the bone hole) into which it is positioned, resulting in frictional engagement or gripping the wall of the bone, which is referred to herein as the expanded deployed state.

As with the prior embodiment, the present invention achieves secure, tensioned attachment of soft tissue to a bone mass using the all-suture anchor assembly 210 as described above in conjunction with an adjustable self-locking device 232 composed of a length of suture 234 passing through a clinching portion 236 in such a way that first and second suture loop members 242, 244 are created. The adjustable self-locking device 232 is the same as that disclosed above with reference to FIGS. 1 to 4.

With reference to FIG. 7, the adjustable self-locking device 232 of this embodiment is preformed to include a double loop configuration having first and second loop members 242, 244 that each traverse a path from one end of the clinching portion 236 to the other end thereof. The adjustable self-locking device 232 is formed by passing the first end 246 of the suture through the clinching portion 236 and similarly passing the second end 252 through the clinching portion 236. In various aspects, the passageway defined by the clinching portion 236 is formed during a braiding process.

Passing ends 246, 252 through the passageway defined by the clinching portion 236 forms the first and second loop members 242, 244. The first and second loop members 242, 244 define mounting portions 256, 258 of the adjustable self-locking device 232 and can be disposed generally opposite from the clinching portion 236.

The longitudinal and parallel placement of the first and second ends 246, 252 of the suture 234 within the clinching portion 236 resists the reverse relative movement of the first and second ends 246, 252 of the adjustable self-locking device 232 once it is tightened. The tensioning of the first and second ends 246, 252 causes reciprocal movement of the first and second loop members 242, 244 relative to clinching portion 236. Upon applying tension to the first and second ends 246, 252, the first and second loop members 242, 244 are reduced to a desired size or placed in a desired tension. Tension in the first and second loop members 242, 244 causes the body of the suture defining the clinching portion 236 to be placed in tension and therefore cause the clinching portion 236 to constrict about the portions 262, 264 of the suture 234 passing through the passageway defined by the clinching portion 236. This constriction causes the adjustable self-locking device 232 to "automatically" lock in a reduced size or smaller diameter configuration.

In accordance with the present method, the adjustable self-locking device 232 is first passed through the soft tissue one wishes to secure to a bone mass. Referring to FIG. 7, the adjustable self-locking device 232, in particular, the first loop member 242 thereof is drawn through the soft tissue with a surgical needle. The second loop member 244 is passed through the soft tissue. In particular, the first loop member 242 and second loop member 244 are pulled through the soft tissue until the two mounting portions 256, 258 defined by the first and second loop members 242, 244 are of substantially the same size and in alignment. As shown in FIG. 7, the first and second end 246, 252 of the suture 234, which function as tension members as will be discussed below in greater detail, of the adjustable self-locking device 232 also extends from one of the first and second loop members 242, 244 and are similarly accessible from outside of the joint under repair.

With the first and second loop members 242, 244 of the adjustable self-locking device 232 outside of the joint, and with reference to FIG. 8, the suture strand loop 222 of the capture member 217 passed through the openings 270, 272 respectively defined by the opposed first and second loop members 242, 244. That is, the free end of the suture strand loop 222 is drawn through the openings 270, 272 such that the suture strand loop 222 is intertwined or linked with the opposed first and second loop members 242, 244. (As described above, the first and second loop members 242, 244 can be linked to two separate all-suture anchor assemblies 210 and attached to bone in two separate locations). In this arrangement, the clinching portion 236 of the adjustable self-locking device 232 between the first and second loop members 242, 244 is in direct contact with the soft tissue securing the suture strand loop 222 to the soft tissue such that the first and second loop members 242, 244 may simultaneously pull against the suture strand loop 222 without fear that the adjustable self-locking device 232 will become disengaged with the soft tissue.

Thereafter, the free end of the suture strand loop 222 is captured by the catch member 223 of the capture member 217; that is, the free end of the suture strand loop 222 is captured, entangled, coupled to, or otherwise attached to the catch member 223 at the first end of the capture member 217 for manipulation of the suture strand loop 222 and ultimately fixed attachment of the free end of the suture strand loop 222 to the catch member 223 at the first end of the capture member 217 upon deployment of the all-suture anchor assembly 210 within the bone mass to which the soft tissue is secured. It is appreciated that if the catch member 223 is not positioned at the first end of the capture member 217 anchor member 214, the free end of the suture strand loop 222 would be fixed wherever the catch member 223 is located.

With the suture strand loop 222 passed through the openings 270, 272 defined by the opposed first and second loop members 242, 244 and the free end of the suture strand loop 222 captured by the catch member 223 at the first end of the capture member 217, the suture strand loop 222 is linked to the first and second loop members 242, 244 and ultimately the soft tissue. Referring to FIG. 8, the all-suture anchor assembly 210 is then inserted into the bone, either directly or within a predrilled hole in the bone mass. The provision of the clinching portion 236 with the suture portions 262, 264 therethrough and under the control of the first and second ends 246, 252 of the suture 234, adjustment in the size of the first and second loop members 242, 244 provided for. This adjustability is useful in several aspects of the surgical procedure.

With the all-suture anchor assembly 210 securely held within the drill hole, the first and second ends 246, 252 of the suture 234 are pulled in a manner reducing the sizes of the first and second loop members 242, 244, and also tensioning the adjustable self-locking device 232, thereby drawing the soft tissue toward the bone mass in a controlled manner. It should be appreciated the ability to pull the first and second loop members 242, 244 relative to the suture strand loop 222 is permitted as a result of the fact that the engagement point for the first and second loop members 242, 244 and the suture strand loop 222 sits above the bone hole and there is not impediments of the free movement of the first and second loop members 242, 244 relative to the suture strand loop 222.

In particular, the first and second ends 246, 252 are pulled in a direction away from the first and second loop members 242, 244 causing the suture 234 to be drawn through the adjustable self-locking device 232 reducing the size of the first and second loop members 242, 244, and also tensioning the adjustable self-locking device 232 to lock the suture portions 262, 264 therein, and consequently drawing the soft tissue toward the bone mass since the size of the suture strand loop 222 is fixed. The first and second ends 246, 252 of the suture 234 are pulled and the sizes of the first and second loop members 242, 244 are reduced until such a time that the soft tissue is fully pulled toward the bone mass. The procedure may be repeated depending upon the needs of the procedure. The excess suture material of the first and second ends 246, 252 of the suture 234 may then be cut away and the incision closed.

As with the embodiment disclosed with reference to FIGS. 1 to 4, the above embodiment may be combined with an anchor sleeve as may be determined by the medical practitioner making using the present system.

In accordance with yet another embodiment as shown with reference to FIGS. 9 to 15, the all-suture anchor assembly 310 further includes a suture capture assembly that is integrated onto with the all-suture anchor 311, thereby obviating the need for the capture members as discussed above with reference to FIGS. 1 to 8.

The all-suture anchor assembly 310 includes the all-suture anchor 311 that is composed of at least one suture strand 313, the all-suture anchoring element 315, and a suture strand loop 314. In accordance with a disclosed embodiment, the suture strand loop 314 is formed by creating a knot 318 (or other enlargement) with the ends of the suture forming the suture strand loop 314. As will be appreciated based upon the following disclosure, knot 318 (or some enlargement) allows the suture strand loop 314 to be captured and fixed distal to the deployed all-suture anchor 311 such that the knot 318 (or enlargement) is be fixed within the bone. The all-suture anchor assembly 310 also includes an all-suture anchoring element 315 threaded along the suture strand 313 in a manner discussed below in greater detail. The all-suture anchor assembly 310 also includes a suture loop capture assembly 317 integrated with the delivery inserter 325 for controlled capture of various elements in a manner discussed below in greater detail.

The all-suture anchoring element 315 is preferably composed solely of an enlarged piece of cylindrical suture material, a suture tape, or a suture sock (as described above). As with the prior embodiments, the enlarged surface area of the all-suture anchoring element 315 allows for the passage of the suture strand 313 therethrough in a manner providing for entanglement of the all-suture anchoring element 315 and the suture strand 313. The enlarged surface area of the all-suture anchoring element 315 also allows for the passage of the suture strand loop 314 therethrough in a manner providing for entanglement and the creating of a locked loop for purposes that will be described below in greater detail. The suture anchoring element 315 includes a first end and a second end, as well as a thickness, a width, and a length along a longitudinal axis. As briefly mentioned above, the all-suture anchor assembly 310 includes the suture strand 313, which is passed through, or weaved through, the all-suture anchoring element 315 at various locations along the length of the all-suture anchoring element 315 (so as to define the all-suture anchor 311). That is, the suture strand 313 penetrates and traverses the all-suture anchoring element 315 to define apertures in the all-suture anchoring element 315.

While the suture strand 313 is disclosed above as being threaded through the all-suture anchoring element 315, it is appreciated that the suture strand could be passed through a central passageway defined by the all-suture anchoring element where the all-suture anchoring element is constructed as an elongated cylindrical member Similar, and while the embodiment above discloses the all-suture anchoring element 315 as having separate ends, the ends of the all-suture anchoring element could certainly be connected as is known in the art.

With the foregoing in mind, it is appreciated that a large variety of constructions and materials will work for the all-suture anchoring element. For example, the all-suture anchor may take a variety of forms as known in the art, for example, ConMed Y-Knot® & Y-Knot® RC, Parcus Draw Tight™, Smith & Nephew Suturefix Ultra, Smith & Nephew Q-FIX®, Zimmer Biomet: JuggerKnot® Soft Anchor; Cayenne Medical (Zimmer Biomet company) SureLock®, and Stryker® Iconix.

The all-suture anchor assembly 310 further includes the suture strand loop 314 and a suture capture assembly 317 integrated into the tip of the delivery inserter 325 for creation of a loop as described below in detail.

The delivery inserter 325 is operated by a surgeon whereby the surgeon manipulates the all-suture anchoring element 315, the suture strand 313, the suture strand loop 314, and the suture capture assembly 317 of the delivery inserter. With the suture stand loop 314, in particular, the knot 318 of the suture strand loop 314, coupled to the suture capture assembly 317 of the delivery inserter, the surgeon inserts the suture strand loop 314, the suture capture assembly 317, the all-suture anchoring element 315, and the entangled portion of the suture strand 313 in the bone hole by pushing the distal second end of the delivery inserter 325 into the bone hole. At that point, the surgeon can push a button or turn a device on the delivery inserter 325 which enables the deployment of the all-suture anchoring element 315. The all-suture anchoring element 315 is then folded, bent, creased, crinkled, bunched, or otherwise changed in shape after it is inserted into the bone hole in a manner that increases the size of the all-suture anchoring element 315 in a manner known to those skilled in the art and as described above.

The suture strand 313, the suture strand loop 314, the all-suture anchoring element 315, and the suture capture assembly 317 are installed within the bone hole in an elongated fashion to take advantage of a small diameter configuration, referred to herein as an undeployed state or installation state. Deployment occurs after the delivery inserter 325 is manipulated such that the capture assembly 317 captures and retains the knot 318 at one end of the suture strand loop 314. The suture strand loop 314 is retained in the bone due to the knot 318 (or some enlargement in the loop 314) that is captured and, therefore, maintained distal to the deployed all-suture anchoring element 315. This capture and retention are followed by positioning of the suture strand 313, the suture strand loop 314, the all-suture anchoring element 315, and the knot 318 within a bone hole for retention of the various elements to a bone mass.

In particular, the all-suture anchor 311 is deployed causing the all-suture anchoring element 315 to fold, bend, crease, crinkle, bunch or otherwise change shape in a manner that compresses the all-suture anchoring element 315. It is appreciated that deployment may occur before, after, or as the delivery inserter 325 is removed. As the all-suture anchoring element 315 is compressed it ultimately increases in size in a direction substantially perpendicular to the longitudinal axis of the bone hole (or otherwise oriented to contact side walls of the bone hole) and develops an outwardly directed force that is directed at the walls of the bone hole. As such, and after the delivery inserter 325, or other delivery instrument, has been removed, the all-suture anchoring element 315 exhibits an outward bias resulting in expansion of the all-suture anchoring element 315 in a direction substantially perpendicular to the longitudinal axis of the bone hole (or otherwise oriented to contact side walls of the bone hole) into which it is positioned, resulting in frictional engagement or gripping the wall of the bone, which is referred to herein as the expanded deployed state. As explained above, this increase in size holds the restrained end of the suture strand loop 314 within the bone hole with a portion of the suture strand loop sitting outside of the bone hole. It should also be noted the knot 318 or expansion on the suture strand loop 314 will aid to restrain the end of the suture strand loop 314 within the bone hole by increasing the force required for the suture strand loop 314 to be withdrawn past the deployed all-suture anchoring element 315.

As with the prior embodiment, the present invention achieves secure, tensioned attachment of soft tissue to a bone mass using the all-suture anchor assembly 310 as described above in conjunction with an adjustable self-locking device 332 composed of a length of suture 334 passing through a nonadjustable clinching portion 336 in such a way that first and second suture loop members 342, 344 are created. The adjustable self-locking device 332 is the same as that disclosed above with reference to FIGS. 1 to 4.

Figure 10:
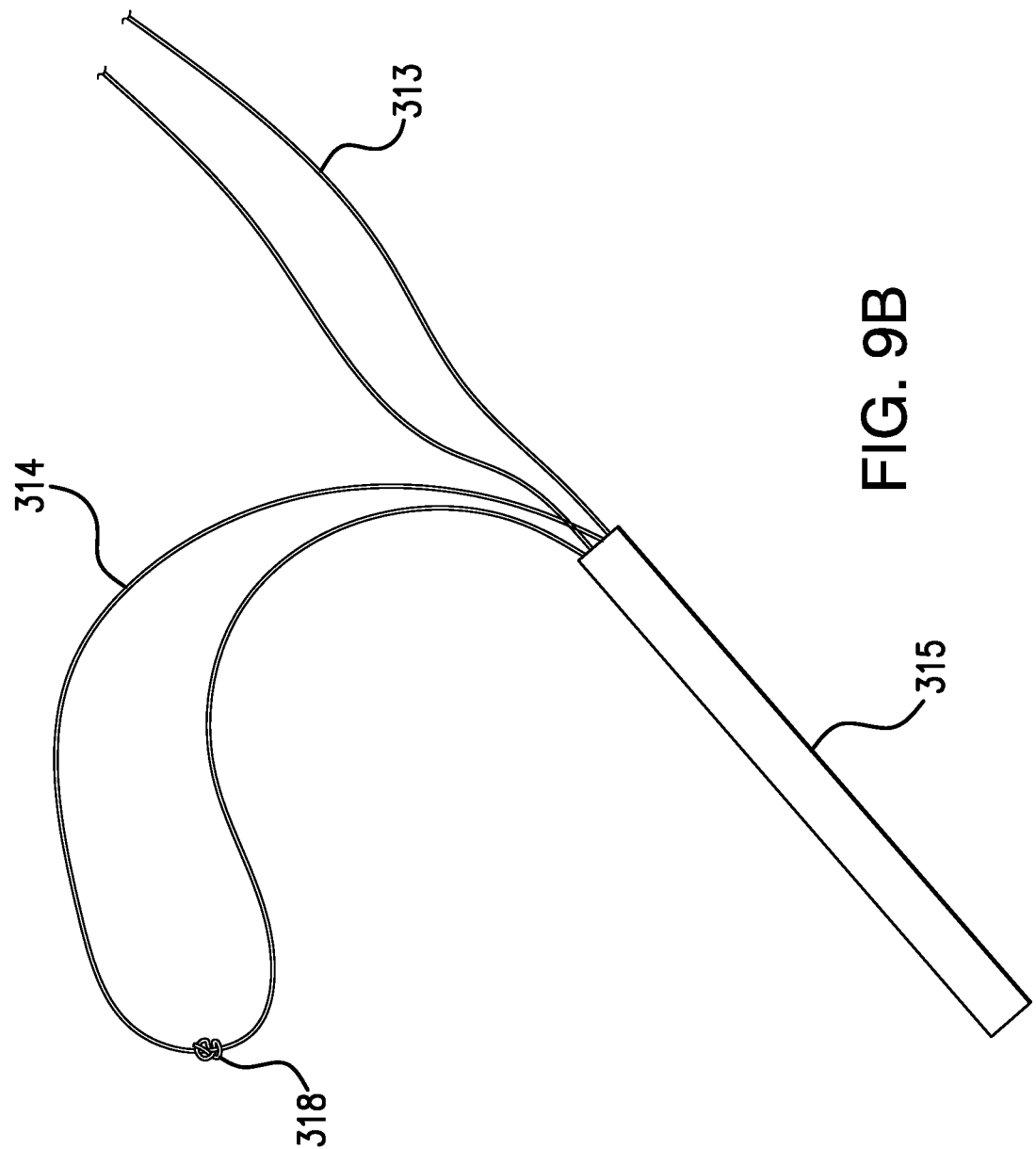
FIG. 10 is a schematic of an adjustable self-locking device in accordance with the third embodiment.

With reference to FIG. 10, the adjustable self-locking device 332 of this embodiment is preformed to include a double loop configuration having first and second loop members 342, 344 that each traverse a path from one end of the nonadjustable clinching portion 336 to the other end thereof. The adjustable self-locking device 332 is formed by passing the first end 346 of the suture through the nonadjustable clinching portion 336 and similarly passing the second end 352 through the nonadjustable clinching portion 336. In various aspects, the passageway defined by the nonadjustable clinching portion 336 is formed during a braiding process.

Passing ends 346, 352 through the passageway defined by the nonadjustable clinching portion 336 forms the first and second loop members 342, 344. The first and second loop members 342, 344 define mounting portions 356, 358 of the adjustable self-locking device 332 and can be disposed generally opposite from the nonadjustable clinching portion 336.

The longitudinal and parallel placement of the first and second ends 346, 352 of the suture 334 within the nonadjustable clinching portion 336 resists the reverse relative movement of the first and second ends 346, 352 of the adjustable self-locking device 332 once it is tightened. The tensioning of the first and second ends 346, 352 causes reciprocal movement of the first and second loop members 342, 344 relative to nonadjustable clinching portion 336. Upon applying tension to the first and second ends 346, 352, the first and second loop members 342, 344 are reduced to a desired size or placed in a desired tension. Tension in the first and second loop members 342, 344 causes the body of the suture defining the nonadjustable clinching portion 336 to be placed in tension and therefore cause the nonadjustable clinching portion 336 to constrict about the portions 362, 364 of the suture 334 passing through the passageway defined by the nonadjustable clinching portion 336. This constriction causes the adjustable self-locking device 332 to "automatically" lock in a reduced size or smaller diameter configuration.

Figure 11:
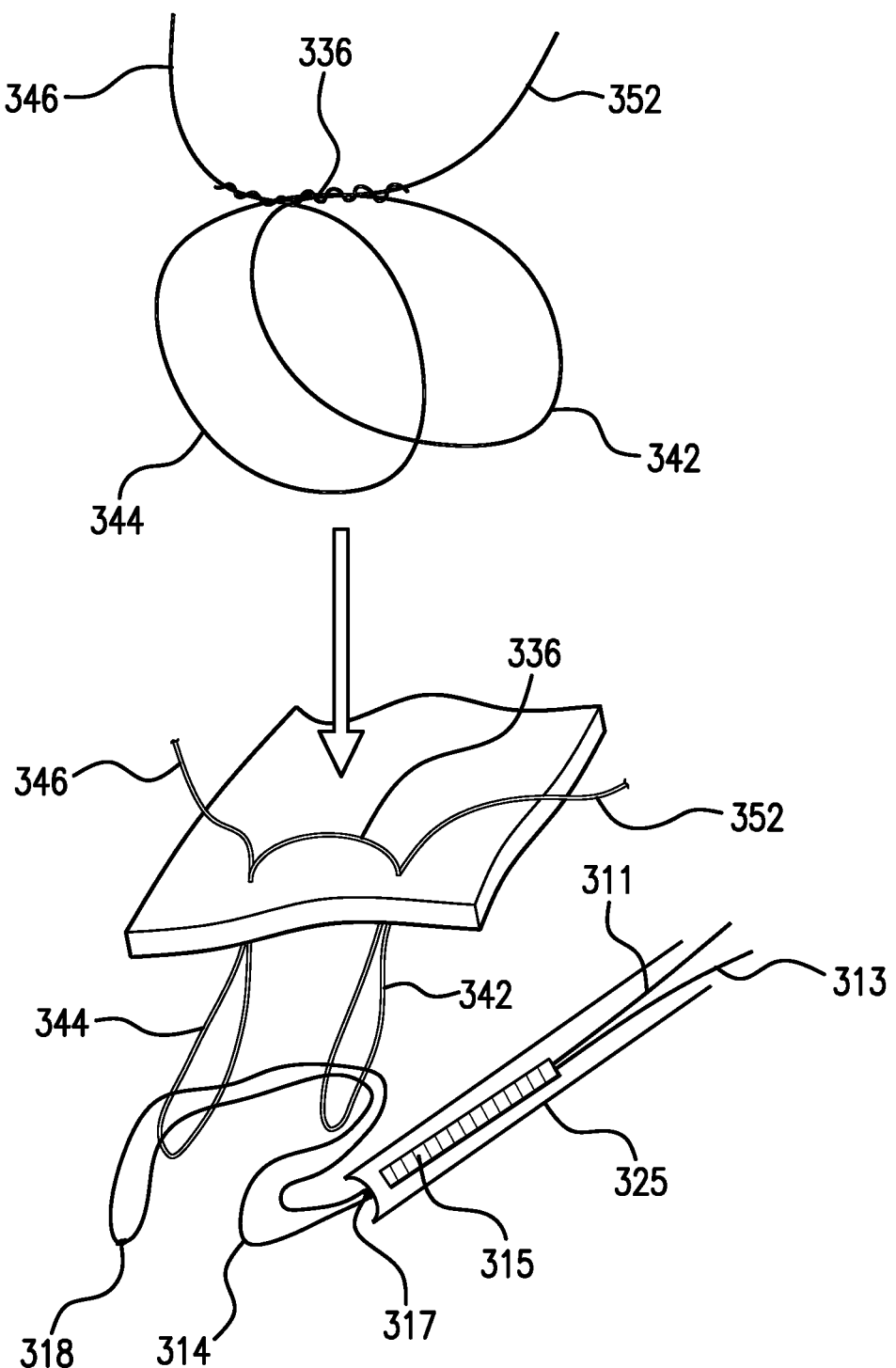
FIGS. 11 to 15 show use of the third embodiment.

In accordance with the present method, and with reference to FIGS. 11 to 15, the adjustable self-locking device 332 is first passed through the soft tissue one wishes to secure to a bone mass. Referring to FIG. 11, the adjustable self-locking device 332, in particular, the first loop member 342 thereof is drawn through the soft tissue with a surgical needle. The second loop member 344 is passed through the soft tissue. In particular, the first loop member 342 and second loop member 344 are pulled through the soft tissue until the two mounting portions 356, 358 defined by the first and second loop members 342, 344 are of substantially the same size and in alignment. As shown in FIGS. 11, the first and second end 346, 352 of the suture 334, which function as tension members as will be discussed below in greater detail, of the adjustable self-locking device 332 also extends from one of the first and second loop members 342, 344 and are similarly accessible from outside of the joint under repair.

With the first and second loop members 342, 344 of the adjustable self-locking device 332 outside of the joint, and with reference to FIG. 11, the suture strand loop 314 (and knot 318 (or enlargement) on the suture strand loop 314) is passed through the openings 370, 372 respectively defined by the opposed first and second loop members 342, 344 such that the suture stand loop 314 is intertwined or linked with the opposed first and second loop members 342, 324. In this arrangement, the nonadjustable clinching portion 336 of the adjustable self-locking device 332 between the first and second loop members 342, 344 is in direct contact with the soft tissue securing the suture strand loop 314 to the soft tissue such that the first and second loop members 342, 344 may simultaneously pull against the suture strand loop 314 without fear that the adjustable self-locking device 332 will become disengaged with the soft tissue.

Figure 12:
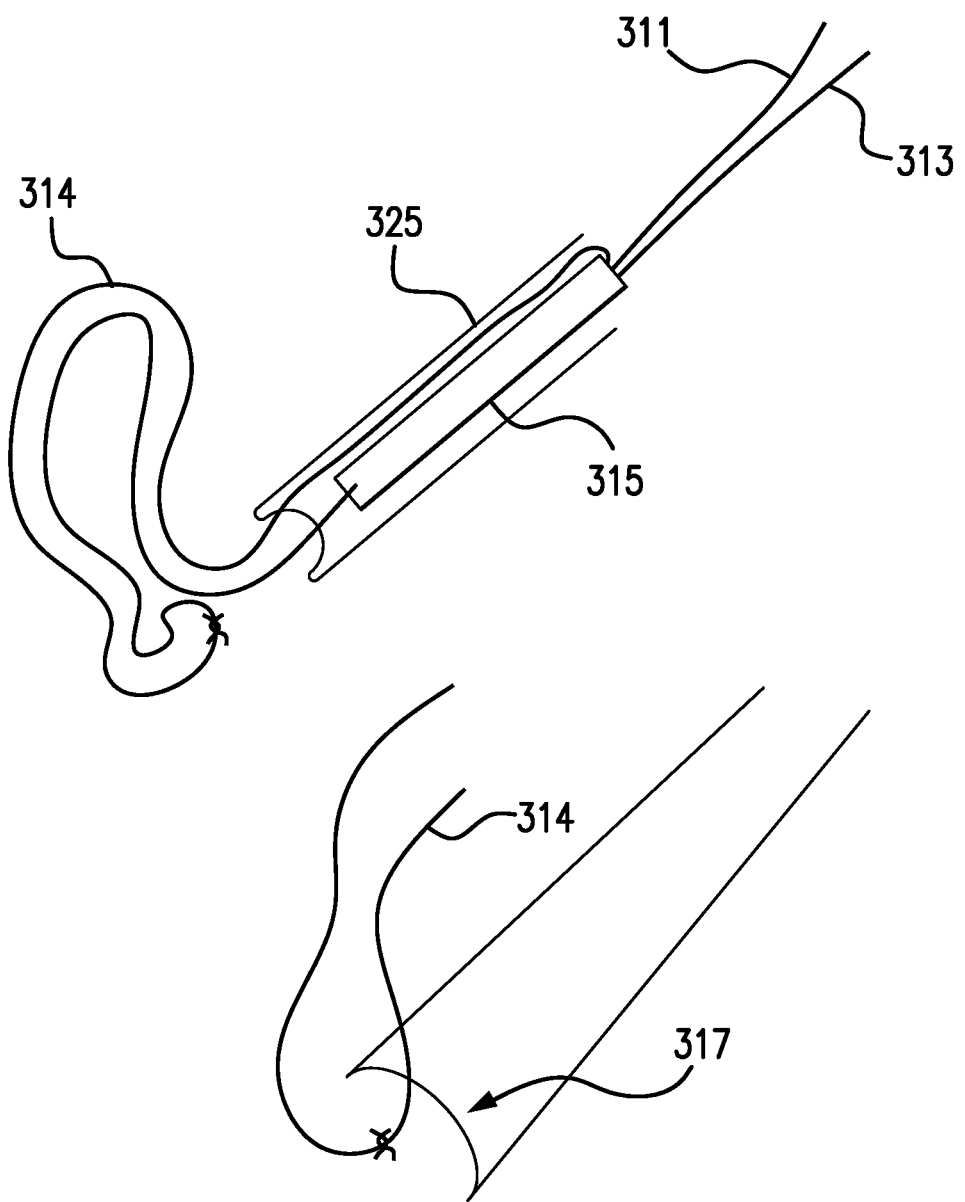

Thereafter, and with reference to FIG. 12, the loop end of the suture strand loop 314 is captured (preferably the knot 318 (or expansion) that creates the loop end of the suture strand loop 314 is captured by the capture assembly 317 of the delivery inserter 325); that is, the loop end of the suture strand loop 314 is captured, entangled, coupled to, or otherwise attached to the capture assembly 317 of the delivery inserter 325 for manipulation of the suture strand loop 314 and ultimately fixed attachment of the loop end of the suture strand loop 314 within the bone hole upon deployment of the all-suture anchor assembly 310 within the bone mass to which the soft tissue is secured. The delivery inserter 325, with the attached capture assembly 317 of the delivery inserter 325, are removed before, during, or after deployment of the all-suture anchor assembly 311 within the bone mass. The knot 318 that is used to create the suture strand loop 314 also provides increased resistance and maintains the suture strand loop 314 distal to the deployed all-suture anchoring element 315 and, therefore, securely within the bone mass.

Figure 13:
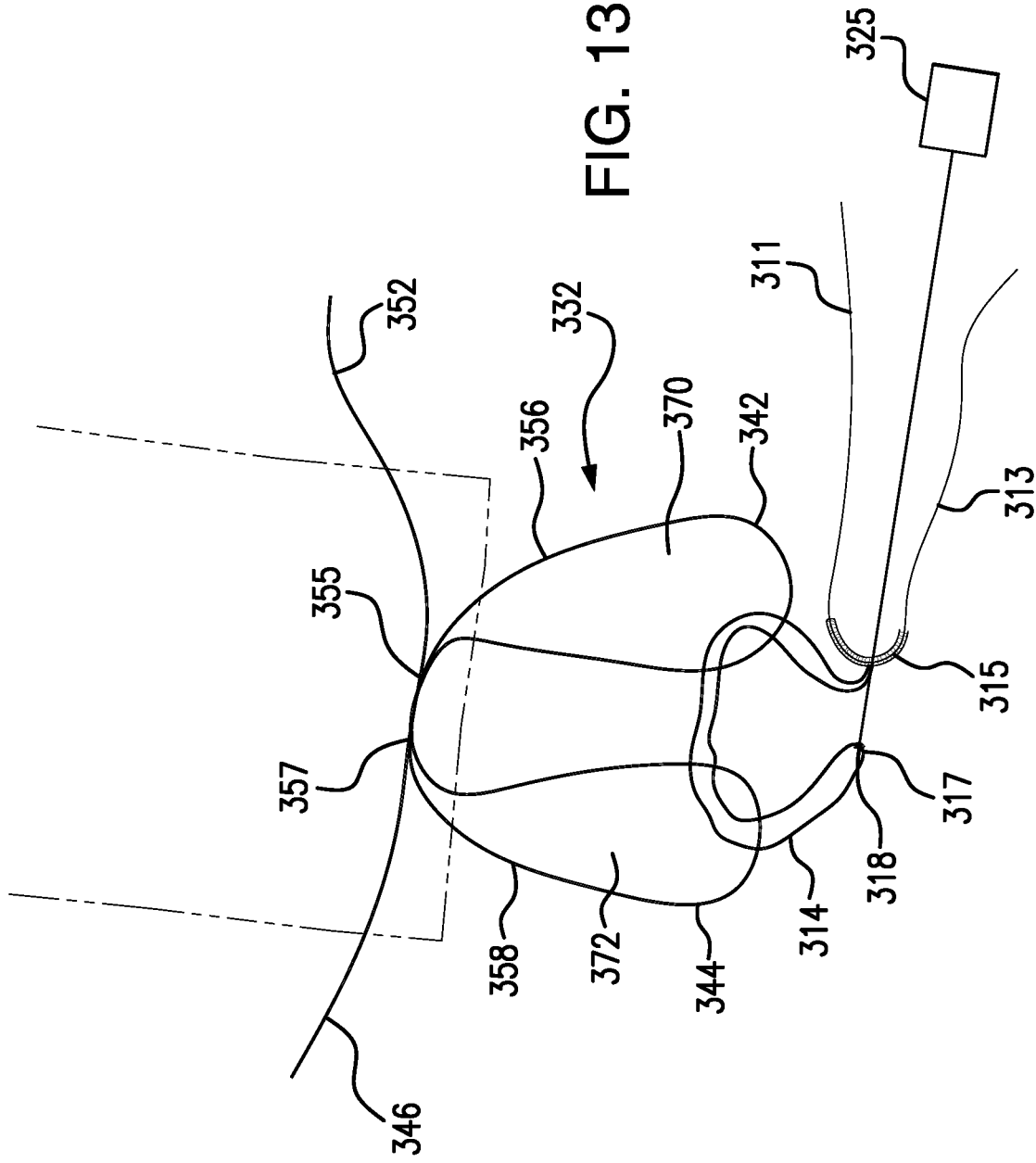
Figure 14:
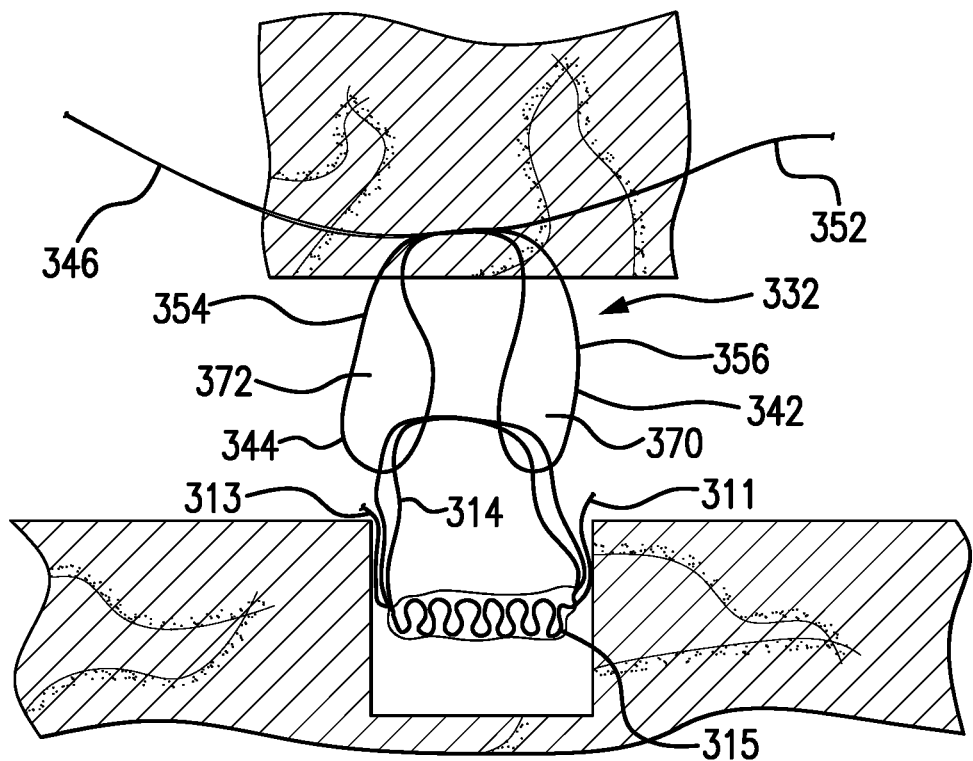
Figure 15:
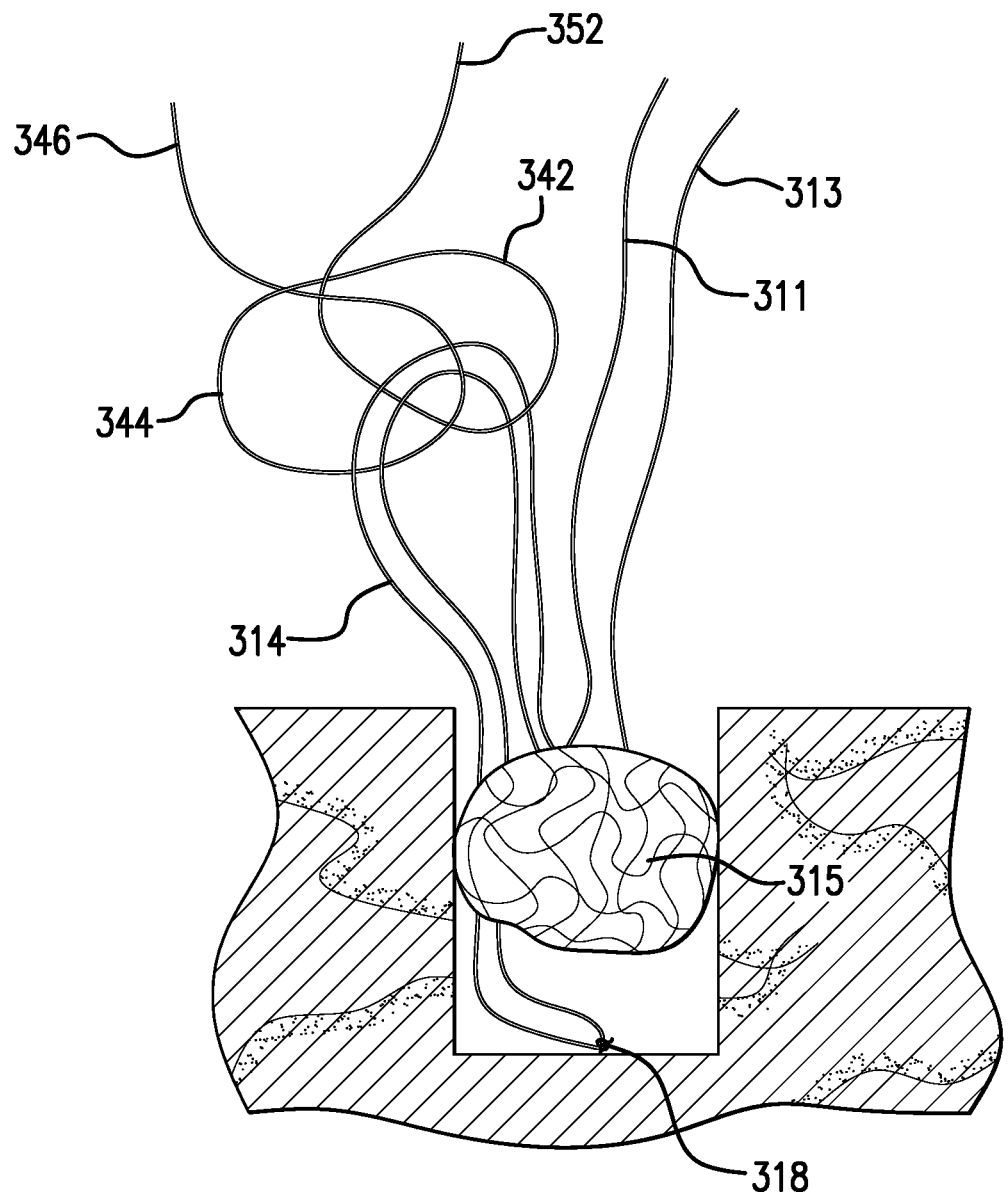

Referring to FIGS. 13, with the suture strand loop 314 passed through the openings 370, 372 defined by the opposed first and second loop members 342, 344 and the loop end of the suture strand loop 314 captured by capture assembly 317 of the delivery inserter 325, the suture strand loop 314 is linked to the first and second loop members 342, 344 and ultimately the soft tissue. Referring to FIGS. 14 and 15, the all-suture anchor assembly 310 is then inserted into the bone mass, either directly or within a predrilled anchor hole in the bone mass. The provision of the nonadjustable clinching portion 336 with the suture portions 362, 364 therethrough and under the control of the first and second ends 346, 352 of the suture 334, adjustment in the size of the first and second loop members 342 and 344 provided for. This adjustability is useful in several aspects of the surgical procedure.

With the all-suture anchor assembly 310 securely held within the drill hole, the first and second ends 346, 352 of the suture 334 are pulled in a manner reducing the sizes of the first and second loop members 342, 344, and also tensioning the adjustable self-locking device 332, thereby drawing the soft tissue toward the bone mass in a controlled manner. It should be appreciated the ability to pull the first and second loop members 342, 344 relative to the suture strand loop 314 is permitted as a result of the fact that the engagement point for the first and second loop members 242, 244 and the suture strand loop 314 sits above the deployed all-suture anchoring element 315 or above the bone hole and there are not impediments of the free movement of the first and second loop members 342, 344 relative to the suture strand loop 314.

In particular, the first and second ends 346, 352 are pulled in a direction away from the first and second loop members 342, 344 causing the suture 334 to be drawn through the adjustable self-locking device 332 reducing the size of the first and second loop members 342, 344, and also tensioning the adjustable self-locking device 332 to lock the suture portions 362, 364 therein, and consequently drawing the soft tissue toward the bone mass since the size of the suture strand loop 322 is fixed. The first and second ends 346, 352 of the suture 334 are pulled and the sizes of the first and second loop members 342, 344 are reduced until such a time that the soft tissue is fully pulled toward the bone mass. The procedure may be repeated depending upon the needs of the procedure. The excess suture material of the first and second ends 346, 352 of the suture 334 may then be cut away and the incision closed.

The system for secure attachment of tissue to bone and other anatomical structure of the present invention as disclosed above with reference to the various embodiments, allows for expanded possibilities in surgical procedures. For example, the system of the present invention is well suited to create a horizontal mattress repair in the soft tissue. In addition, and while the various embodiments disclose an adjustable self-locking device with first and second loop members it is appreciated a plurality of adjustable self-locking devices may be used in combination or an adjustable self-locking device with more than two loop members may be used.

Figure 16:
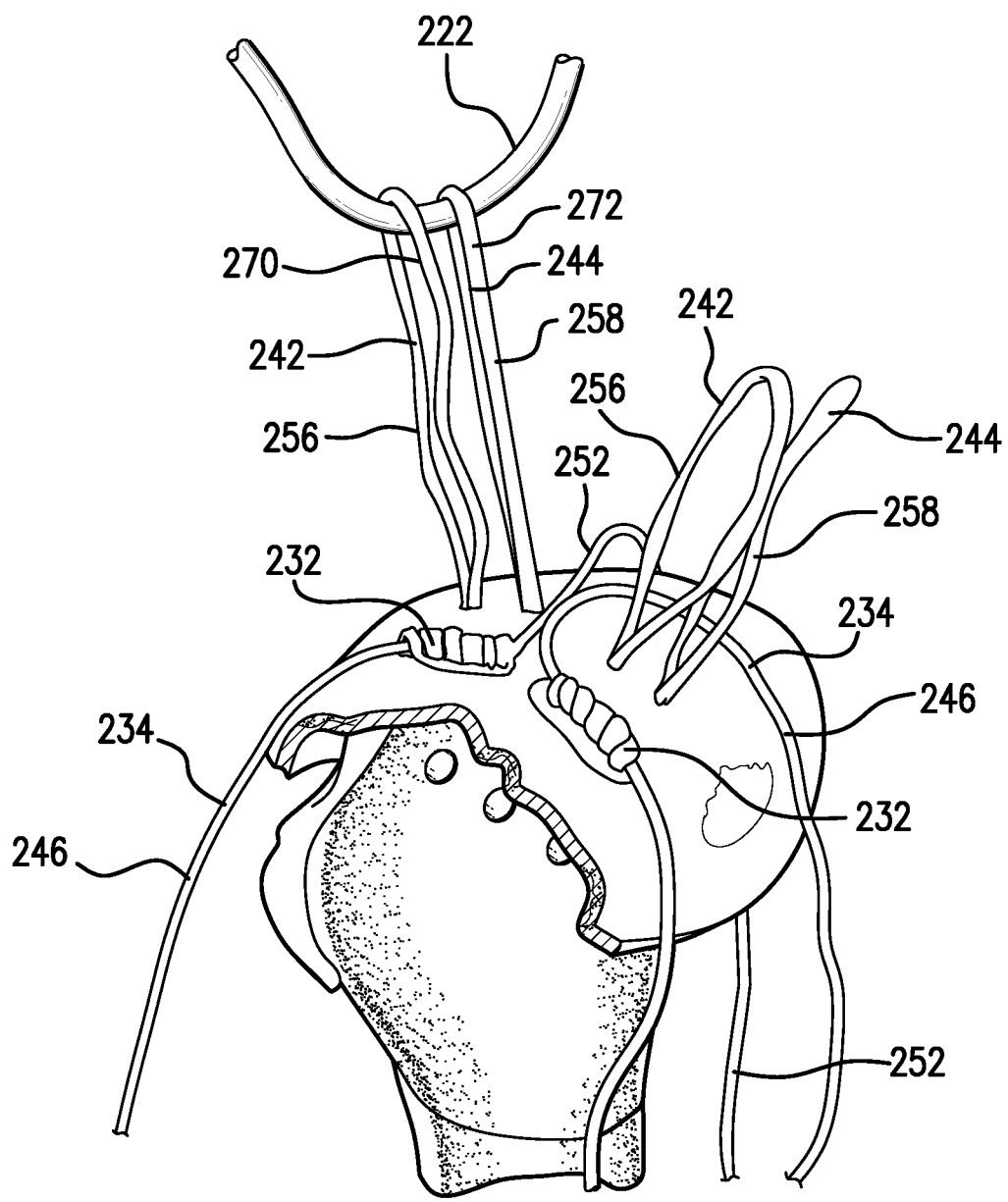
FIGS. 16, 17, and 18 show use of the second embodiment in the performance of a ripstop technique.
Figure 17:
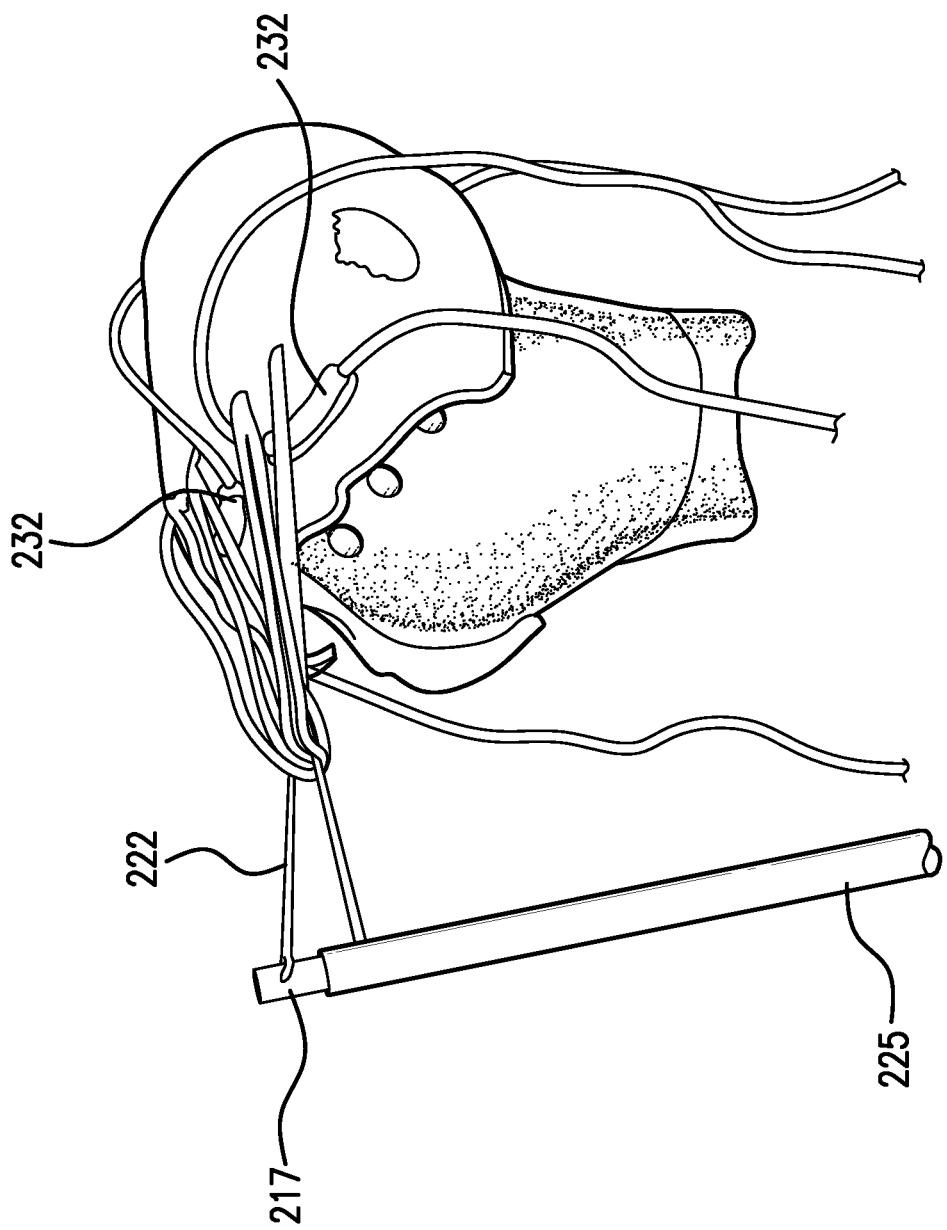
Figure 18:
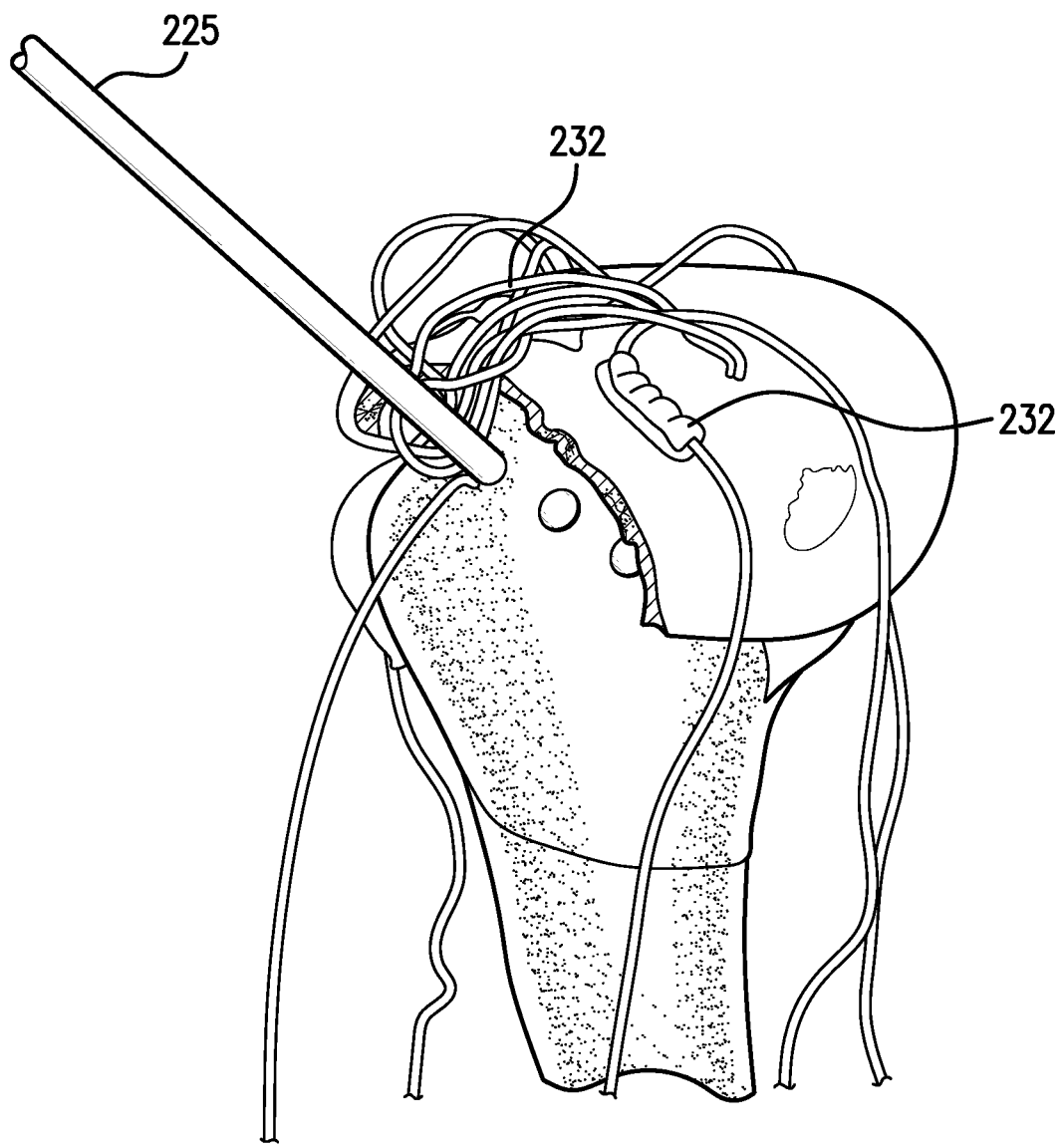

With reference to FIGS. 16, 17, and 18, the present system is used to create a "locking mattress repair" or "ripstop technique." This repair procedure is disclosed below with reference to the embodiment disclosed with reference to FIGS. 6 to 8, although it is appreciated any of the embodiments disclosed herein may be used in conjunction with this methodology.

First and second adjustable self-locking devices 232 are first passed through the soft tissue one wishes to secure to a bone mass. In particular, the first loop members 242 thereof are drawn through the soft tissue with a surgical needle or a suture passing loop. The second loop members 244 are passed through the soft tissue. In particular, the first loop members 242 and second loop members 244 are pulled through the soft tissue until the two mounting portions 256, 258 defined by the first and second loop members 242, 244 are of substantially the same size and in alignment. The first and second ends 246, 252 of the suture 234, which function as tension members as will be discussed below in greater detail, of the adjustable self-locking device 232 also extends from one of the first and second loop members 242, 244 and are similarly accessible from outside of the joint under repair.

The first and second loop members 242, 244 are then again drawn through the soft tissue with a surgical needle at a position removed from the edge of the soft tissue such that the first and second loop member 242, 244 are on the same side of the tissue (that is, the top side for the sake of describing the present procedure) as the clinching portion 236.

With the first and second loop members 242, 244 of the adjustable self-locking device 232 outside of the joint and extending above the top side of the soft tissue at a position remote from the edge of the soft tissue, the suture strand loop 222 is passed through the openings 270, 272 respectively defined by the opposed first and second loop members 242, 244. That is, the free end of the suture strand loop 222 is drawn through the openings 270, 272 such that the suture stand loop 222 is intertwined or linked with the opposed first and second loop members 242, 224. In this arrangement, the clinching portion 236 of the adjustable self-locking device 232 between the first and second loop members 242, 244 is in direct contact with the soft tissue securing the suture strand loop 222 to the soft tissue such that the first and second loop members 242, 244 may simultaneously pull against the suture strand loop 222 without fear that the adjustable self-locking device 232 will become disengaged with the soft tissue.

Thereafter, the free end of the suture strand loop 222 is captured; that is, the free end of the suture strand loop 222 is captured, entangled, coupled to, or otherwise attached to the capture member 217 for manipulation of the suture strand loop 222 and ultimately fixed attachment of the free end of the suture strand loop 222 within the bone hole upon deployment of the all-suture anchor assembly 210 within the bone mass to which the soft tissue is secured.

With the suture strand loop passed through the openings 270, 272 defined by the opposed first and second loop members 242, 244 and the free end of the suture strand loop 222 captured by the capture member 217, the suture strand loop 222 is linked to the first and second loop members 242, 244 and ultimately the soft tissue. Referring to FIG. 13, the first and second loop members 242, 244 are pulled over the clinching portion 236 and the all-suture anchor assembly 210 is inserted into the bone mass, or within an anchor hole predrilled in the bone mass. The 'rip-stop' configuration is created by the first and second loop members 242, 244 being pulled over the clinching portion 236 and provides additional security of suture at the site of the soft tissue repair. The provision of the clinching portion 236 with the suture portions 262, 264 therethrough and under the control of the first and second ends 246, 252 of the suture 234, adjustment in the size of the first and second loop members 242, 244 is provided for. This adjustability is useful in several aspects of the surgical procedure.

With the all-suture anchor assembly 210 securely held within the drill hole, the first and second ends 246, 252 of the suture 234 are pulled in a manner reducing the sizes of the first and second loop members 242, 244, and also tensioning the adjustable self-locking device 232, thereby drawing the soft tissue toward the bone mass in a controlled manner. It should be appreciated the ability to reduce the sizes of the first and second loop members 242, 244 is permitted as a result of the fact that the engagement point for the first and second loop members 242, 244 and the suture strand loop 222 sits above the deployed all-suture anchoring element 215, or above the bone hole, and there are not impediments of the free movement of the first and second loop members 242, 244 relative to the suture capture member 217.

In particular, the first and second ends 246, 252 are pulled in a direction away from the first and second loop members 242, 244 causing the suture 234 to be drawn through the adjustable self-locking device 232 reducing the size of the first and second loop members 242, 244, and also tensioning the adjustable self-locking device 232 to lock the suture portions 262, 264 therein, and consequently drawing the soft tissue toward the bone mass since the size of the suture strand loop 222 is fixed. The first and second ends 246, 252 of the suture 234 are pulled and the first and second loop members 242, 244 size is reduced until such a time that the soft tissue is fully pulled toward the bone mass. The excess suture material of the first and second ends 346, 352 of the suture 334 may then be cut away and the incision closed.

Figure 19:
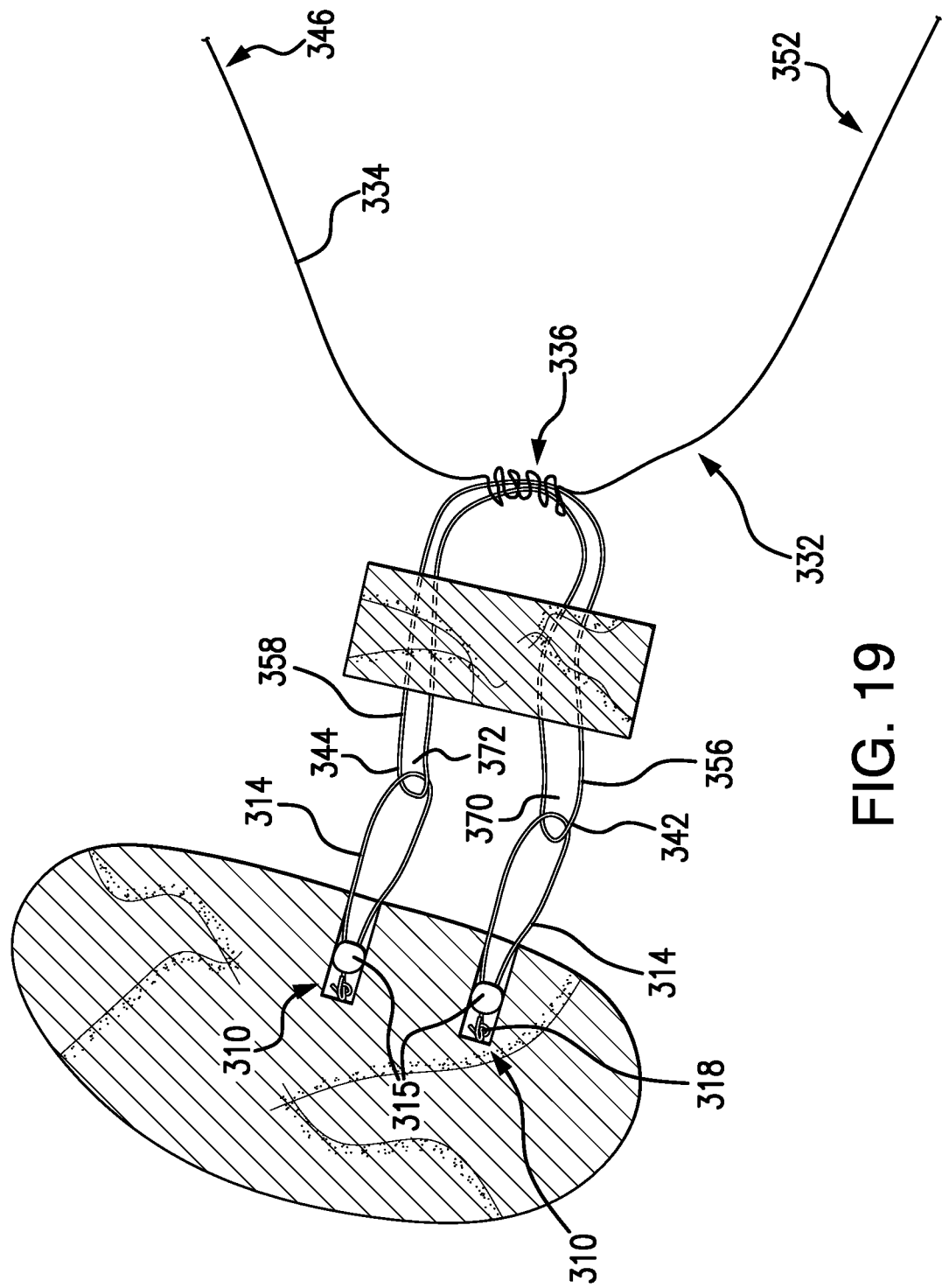
FIG. 19 shows a technique for glenoid bone graft in accordance with the present invention.

With reference to FIG. 19, the present system is used in a glenoid bone grafting procedure. This repair procedure is disclosed below with reference to the embodiment disclosed with reference to FIGS. 9 to 15, although it is appreciated any of the embodiments disclosed herein may be used in conjunction with this methodology.

An adjustable self-locking device 332 is first passed through the bone graft one wishes to secure to the glenoid. In particular, the first loop members 342 thereof is drawn through the bone graft with a surgical needle or a suture passing loop. The second loop members 344 is passed through the bone graft. In particular, the first loop members 342 and second loop members 344 are pulled through the bone graft until the two mounting portions 356, 358 defined by the first and second loop members 342, 344 are of substantially the same size and in alignment. The first and second ends 346, 352 of the suture 334, which function as tension members as will be discussed below in greater detail, of the adjustable self-locking device 332 also extends from one of the first and second loop members 342, 344 and are similarly accessible from outside of the joint under repair.

With the first and second loop members 342, 344 of the adjustable self-locking device 332 outside of the joint, first and second all-suture anchor assemblies 310 are used to secured the first and second loop members 342, 344 to the glenoid. The suture strand loops 314 are respectively passed through the openings 370, 372 defined by the opposed first and second loop members 342, 344.

Thereafter, the knots 318 of the suture strand loops 314 are captured by the capture assembly 317 of the inserter 325 (see FIG. 13) for manipulation of the suture strand loops 314 and ultimately fixed attachment of the suture strand loops 314 within the bone hole upon deployment of the all-suture anchoring elements 315 of the all-suture anchor assemblies 310 within the glenoid. The inserters 325 and capture assemblies 317 have been removed after deployment of the all-suture anchor assemblies 310 and are, therefore, not shown in FIG. 19.

With the all-suture anchor assemblies 310 securely held within the drill hole, the first and second ends 346, 352 of the suture 334 are pulled in a manner reducing the sizes of the first and second loop members 342, 344, and also tensioning the adjustable self-locking device 332, thereby drawing the bone graft toward the glenoid in a controlled manner. It should be appreciated the ability to reduce the size of the first and second loop members 342, 344 is permitted as a result of the fact that the engagement point for the first and second loop members 342, 344 and the suture strand loops 314 sit above the deployed all-suture anchoring element 315, or above the bone hole, and there are not impediments to the free movement of the first and second loop members 342, 344 relative to the suture strand loop 314.

As those skilled in the art will certainly appreciate the glenoid bone grafting procedure described above may be extended to other procedures requiring bone grafts and tissue repairs (for example, labral repairs). Referring to the various embodiments disclosed above, it is described that the excess suture material at the first and second ends (146, 152; 246,252; 346, 352) of the adjustable self-locking device (132, 232, 332) is cut away at the end of the procedure. Alternatively, a dual-row (or transosseous equivalent repair) can be created by anchoring these suture strands (146, 152; 246, 252; or 346, 352) to the bone at another location using a standard knotless suture anchor (such as the Arthrex SwiveLock anchor, Smith & Nephew Footprint Ultra PK Knotless Anchor, Smith & Nephew Healicoil Knotless, or Mitek Healix Advance Knotless Anchor) before cutting the excess suture material. In the case of the glenoid bone graft procedure, the excess suture material at the first and second ends (346, 352) can be passed through the labrum and/or glenohumeral ligament before these suture ends are secured to the glenoid, at another location, using a standard knotless suture anchor.

In many situations throughout the discussion above, the terminology relating to the secure attachment of soft tissue to bone mass has been used. Such terminology refers to the attachment or reattachment of tissue to a bone mass by securely binding the tissue to the bone mass utilizing the novel knotless suture anchor assembly. The suture element can be made up of a known suture material, or it can be made of polymer materials, or can be formed of bioabsorbable/biocomposite material such as a polylactide polymer.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A system for secure attachment of tissue to bone and other anatomical structure, comprising:
   an all-suture anchor assembly including an all-suture anchor having at least one suture strand and an all-suture anchoring element threaded along the suture strand, the all-suture anchor assembly also includes a capture member for controlled capture of various elements, the capture member includes an elongated body having a forward first end including a catch member and a rear second end shaped and dimensioned for selective coupling with a distal second end of a delivery inserter, and the catch member is a lateral slot positioned at the forward first end of the capture member; and
   an adjustable self-locking device including a length of suture passing through at least one clinching portion.

2. The system according to claim 1, wherein the all-suture anchoring element is a cylindrical suture material or a suture tape, and a surface area of the all-suture anchoring element allows for passage of the suture strand therethrough in a manner providing for entanglement of the all-suture anchoring element and the suture strand.

3. The system according to claim 1, wherein the adjustable self-locking device includes first and second loop members that each traverse a path from one end of the clinching portion to the other end of the clinching portion.

4. The system according to claim 3, wherein a first end of the suture passes through the clinching portion and a second end of the suture passes through the clinching portion to form the first and second loop members.

5. The system according to claim 4, wherein longitudinal and parallel placement of the first and second ends of the suture within the clinching portion resists reverse relative movement of the first and second ends of the suture of the adjustable self-locking device once the adjustable self-locking device is tightened.

6. The system according to claim 1, wherein the capture member and the all-suture anchor are constructed in an integral manner.

* * * * *